United States Patent [19]

Higuchi et al.

[11] Patent Number: 5,091,586
[45] Date of Patent: Feb. 25, 1992

[54] NOVEL DIALKYL PEROXIDES, PRODUCTION METHOD AND USE THEREOF

[75] Inventors: Yoshiki Higuchi; Shuji Suyama, both of Chita, Japan

[73] Assignee: Nippon Oil and Fats Company, Limited, Tokyo, Japan

[21] Appl. No.: 550,901

[22] Filed: Jul. 11, 1990

[30] Foreign Application Priority Data

Jul. 19, 1989 [JP] Japan ................. 1-184498
Aug. 25, 1989 [JP] Japan ................. 1-217197
Sep. 5, 1989 [JP] Japan ................. 1-228189

[51] Int. Cl.$^5$ .......................... C07C 49/213
[52] U.S. Cl. ..................... 568/332; 568/337; 568/533; 568/335
[58] Field of Search .......... 568/335, 333, 558, 332, 568/335

[56] References Cited

U.S. PATENT DOCUMENTS 3,755,454  8/1973  Chang et al. ............... 568/558
4,416,826  11/1983  Neckers ..................... 549/410
4,486,605  12/1984  Harada et al. .............. 568/335
4,864,064  9/1989  Hogel ........................ 568/558

FOREIGN PATENT DOCUMENTS 59-197401  11/1984  Japan ....................... 560/1

*Primary Examiner*—James H. Reamer
*Attorney, Agent, or Firm*—Stevens, Davis, Miller & Mosher

[57] ABSTRACT

A novel dialkyl peroxide is represented by a general formula (I):

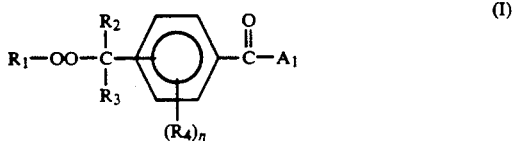

This peroxide is produced by particular methods and used as a photolysis type or pyrolysis type radical forming agent.

3 Claims, 1 Drawing Sheet

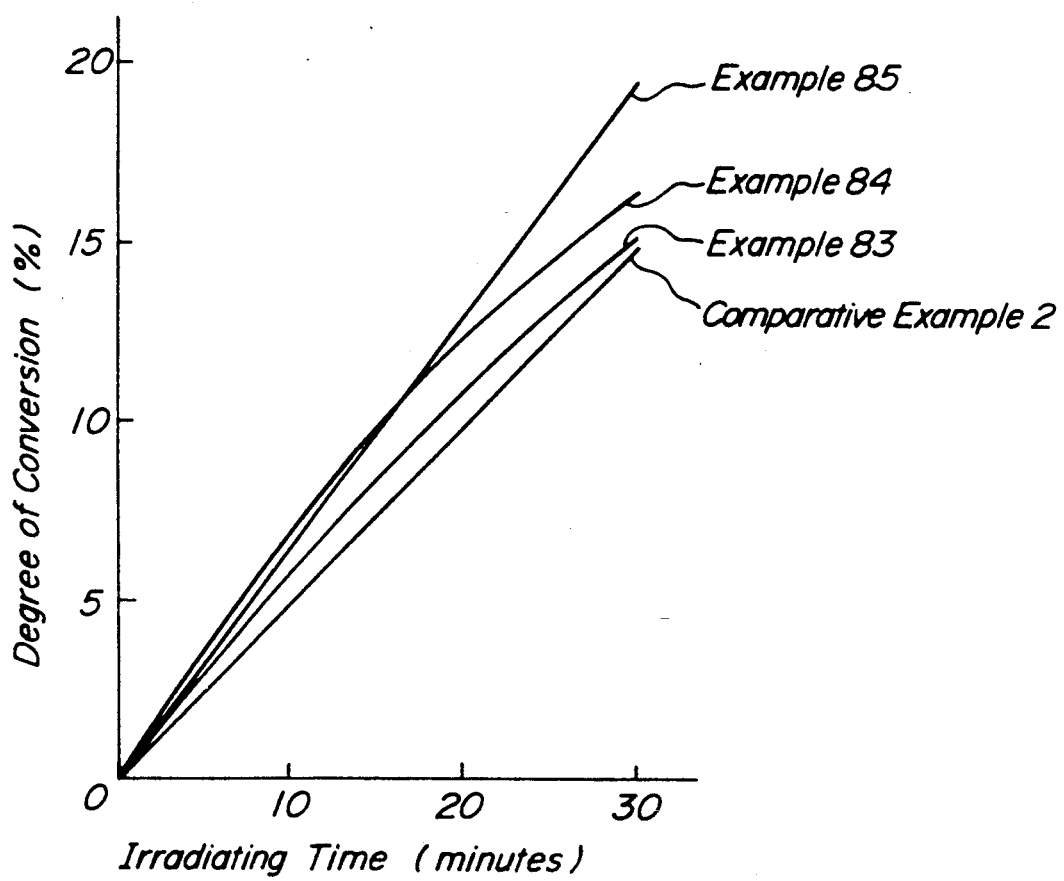
FIG_1

NOVEL DIALKYL PEROXIDES, PRODUCTION METHOD AND USE THEREOF

BACKGROUND OF THE INVENTION

1. Field of the Invention

This invention relates to novel dialkyl peroxides and a method of producing the same as well as a use thereof.

2. Related Art Statement

The photopolymerization or photocuring method for photopolymerizable (photocurable) monomer and photopolymerizable (photocurable) resin composition can rapidly be carried out at a low temperature as compared with thermal polymerization, thermal curing and oxidation curing methods, so that it has many merits such as improvement of productivity, energy-saving, non-pollution and the like. Furthermore, selective curing is made possible. Therefore, the photopolymerization or photocuring method is widely used in application for printing ink, paint, adhesive, resin letterpress, working of printed circuit board and the like.

In the photopolymerization or photocuring method, various initiators have been developed. For example, there are known photopolymerization initiators producing radicals under an influence of ultraviolet ray such as benzoin, benzoin ethers, benzyl, aryldiazonium salt, benzophenone derivatives, acetophenone derivatives, xanthates, thioxanthones, halogenated hydrocarbons and the like [Journal of Oil and Color Chemistry Association, vol. 59, pp 166–171 (1976)].

Furthermore, it is known that organic peroxides such as benzoyl peroxide, di-t-butyl peroxide and the like can be used as a photopolymerization initiator. However, these organic peroxides generally absorb only a light of not more than 320 nm [Chemical Review, vol. 68, pp 125–151 (1965)]. Although it has been attempted to use the organic peroxide together with a photosensitizer, it has been reported that the efficiency of light energy transmitted from the photosensitizer to the organic peroxide is low and the photolysis efficiency of the organic peroxide lowers, and particularly di-t-butyl peroxide as a dialkyl type organic peroxide produces no photosensitized decomposition in its molecule [Journal of the American Chemical Society, vol. 87, pp 3413–3417 (1965)].

In order to solve the above problem, ester-type organic peroxides containing benzophenone group as a light absorbing group in its molecule have been developed (U.S. Pat. No. 4,416,826, Japanese Patent laid open No. 59-197401). However, such a compound has drawbacks that the storing stability in dark room is poor and the cured resin is yellowed.

The above conventional photopolymerization initiators are useful, but have still some drawbacks to be solved. For instance, there are the following problems:

(1) benzoin and benzoin ethers are poor in the storing stability in dark room;

(2) benzophenone derivatives are used together with an amine or the like, but the resulting polymer or cured product is yellowed;

(3) thioxanthones are low in the solubility to monomer or resin; and (4) the ester-type peroxide containing the light absorbing group is poor in the thermal stability and the cured resin is yellowed.

SUMMARY OF THE INVENTION

It is, therefore, an object of the invention to solve the aforementioned drawbacks of the conventional photopolymerization initiators and to provide novel peroxides having good thermal stability and photopolymerization or photocuring efficiency and giving less yellowing of polymer or cured product and high industrial merit as well as a use thereof and a method of producing the same.

The object of the invention has been accomplished by using a novel dialkyl peroxide containing a light absorbing group.

According to a first aspect of the invention, there is the provision of a dialkyl peroxide represented by the following general formula (i):

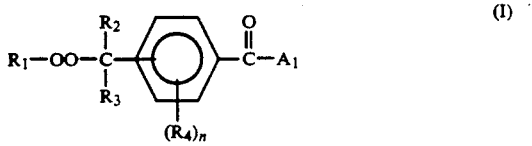

(wherein

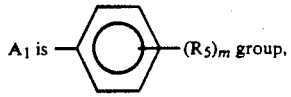 group,

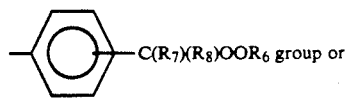 group or

—C(R$_9$)(R$_{10}$)(Z$_1$) group, each of R$_1$ and R$_6$ is a tertiary alkyl group having a carbon number of 4–8 or an α-cumyl group, each of R$_2$, R$_3$, R$_7$ and R$_8$ is an alkyl group having a carbon number of 1–2, R$_4$ is an alkyl group having a carbon number of 1–3 or a hydrogen atom, R$_5$ is an alkyl group having a carbon number of 1–12, an alkoxy group having a carbon number of 1–4, a halogen atom or a hydrogen atom, each of R$_9$ and R$_{10}$ is an alkyl group having a carbon number of 1–4 or R$_9$ and R$_{10}$ form a cycloalkyl group having a total carbon number of 5–8 together, Z$_1$ is a hydroxyl group, a chlorine atom, a bromine atom or an alkoxy group having a carbon number of 1–4, n is 1 or 2, m is an integer of 1–3, and each of R$_1$OOC(R$_2$)(R$_3$) group and R$_6$OOOC(R$_7$)(R$_8$) group is a meta or para position).

According to a second aspect of the invention, there is the provision of a method of producing a dialkyl peroxide represented by the following general formula (I'):

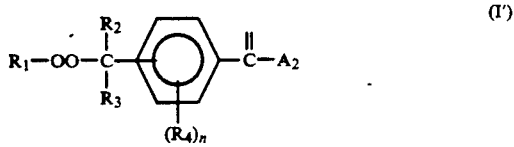

wherein $A_2$ is 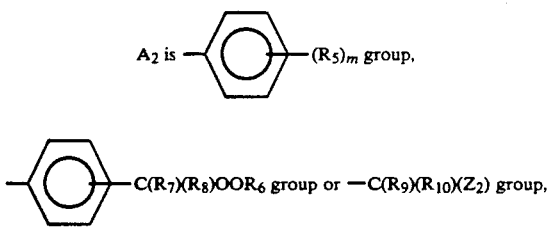 —(R$_5$)$_m$ group,

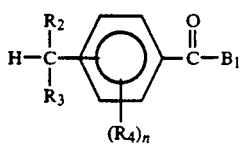—C(R$_7$)(R$_8$)OOR$_6$ group or —C(R$_9$)(R$_{10}$)(Z$_2$) group, each of $R_1$ and $R_6$ is a tertiary alkyl group having a carbon number of 4–8 or an α-cumyl group, each of $R_2$, $R_3$, $R_7$ and $R_8$ is an alkyl group having a carbon number of 1–2, $R_4$ is an alkyl group having a carbon number of 1–3 or a hydrogen atom, $R_5$ is an alkyl group having a carbon number of 1–12, an alkoxy group having a carbon number of 1–4, a halogen atom or a hydrogen atom, each of $R_9$ and $R_{10}$ is an alkyl group having a carbon number of 1–4 or $R_9$ and $R_{10}$ form a cycloalkyl group having a total carbon number of 5–8 together, $Z_2$ is a chlorine atom, a bromine atom or an alkoxy group having a carbon number of 1–4, n is 1 or 2, m is an integer of 1–3, and each of $R_1OOC(R_2)(R_3)$ group and $R_6OOC(R_7)(R_8)$ group is a meta or para position), characterized in that an aromatic ketone containing an isoalkyl group and represented by the following general formula (IV):

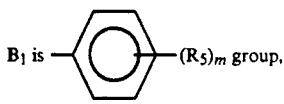 (IV)

wherein $B_1$ is 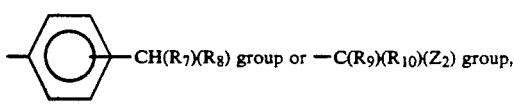

—(R$_5$)$_m$ group,

—CH(R$_7$)(R$_8$) group or —C(R$_9$)(R$_{10}$)(Z$_2$) group, each of $R_2$, $R_3$, $R_4$, $R_5$, $R_7$, $R_8$, $R_9$, $R_{10}$, $Z_2$, n and m is the same as mentioned above, and each of CH(R$_2$)(R$_3$) group and CH(R$_7$)(R$_8$) group is a metha or para position) is reacted with a hydroperoxide represented by the following general formula (II) [and (III)]:

 $R_1OOH \ldots$ (II)

 $R_6OOH \ldots$ (III)

(wherein each of $R_1$ and $R_6$ is the same as mentioned above) in the presence of a salt of metal selected from transition elements of Groups 4 and 5 in the periodic table.

According to a third aspect of the invention, there is the provision of a method of producing a dialkyl peroxide represented by the general formula (I'), characterized in that an aromatic ketone containing α-hydroxy isoalkyl group and represented by the following general formula (V):

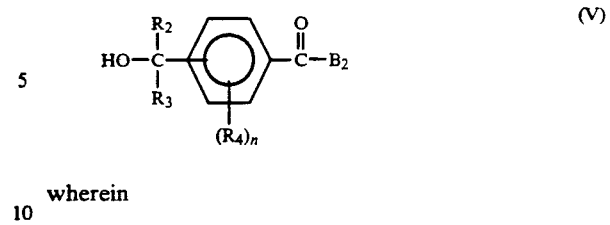 (V)

wherein $B_2$ is  —(R$_5$)$_m$ group,

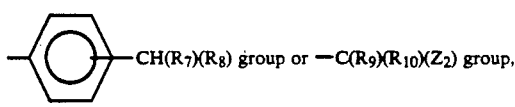—CH(R$_7$)(R$_8$) group or —C(R$_9$)(R$_{10}$)(Z$_2$) group, each of $R_2$, $R_3$, $R_4$, $R_5$, $R_7$, $R_8$, $R_9$, $R_{10}$, $Z_2$, n and m is the same as mentioned above, and each of COH(R$_2$)(R$_3$) group and COH(R$_7$)(R$_8$) group is a metha or para position) is reacted with a hydroperoxide represented by the general formula (II) [and (III)]in the presence of an acid catalyst.

According to a fourth aspect of the invention, there is the provision of a method of producing a dialkyl peroxide represented by the general formula (I'), characterized in that an aromatic ketone containing isoalkenyl group and represented by the following general formula (VI):

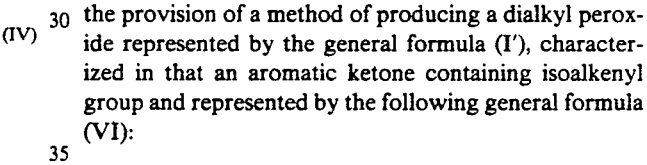 (VI)

wherein $B_3$ is 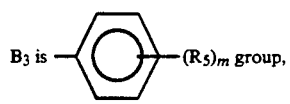 —(R$_5$)$_m$ group,

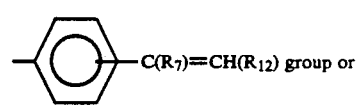—C(R$_7$)=CH(R$_{12}$) group or

—C(R$_9$)(R$_{10}$)(Z$_2$) group, each of $R_{11}$ and $R_{12}$ is a hydrogen atom or a methyl group, each of $R_2$, $R_4$, $R_5$, $R_7$, $R_9$, $R_{10}$, $Z_2$, n and m is the same as mentioned above, and each of C(R$_2$)=CH(R$_{11}$) group and C(R$_7$)=CH(R$_{12}$) group is a metha or para position) is reacted with a hydroperoxide represented by the general formula (II) [and (III)]in the presence of an acid catalyst.

According to a fifth aspect of the invention, there is the provision of a method of producing a dialkyl peroxide represented by the following general formula (I''):

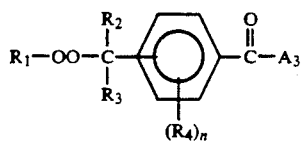

(I'')

wherein

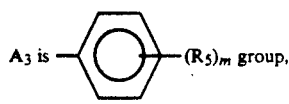

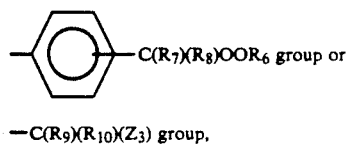

—C(R$_9$)(R$_{10}$)(Z$_3$) group, each of R$_1$ and R$_6$ is a tertiary alkyl group having a carbon number of 4–8 or an α-cumyl group, each of R$_2$, R$_3$, R$_7$ and R$_8$ is an alkyl group having a carbon number of 1–2, R$_4$ is an alkyl group having a carbon number of 1–3 or a hydrogen atom, R$_5$ is an alkyl group having a carbon number of 1–12, an alkoxy group having a carbon number of 1–4, a halogen atom or a hydrogen atom, each of R$_9$ and R$_{10}$ is an alkyl group having a carbon number of 1–4 or R$_9$ and R$_{10}$ form a cycloalkyl group having a total carbon number of 5–8 together, Z$_3$ is a hydroxyl group or an alkoxy group having a carbon number of 1–4, n is 1 or 2, m is an integer of 1–3, and each of R$_1$OOC(R$_2$)(R$_3$) group and R$_6$OOC(R$_7$)(R$_8$) group is a meta or para position), characterized in that an aromatic ketone containing α-halogenated isoalkyl group and represented by the following general formula (VII):

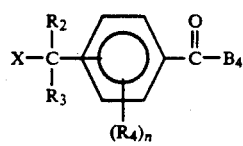

(VII)

wherein

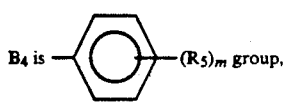

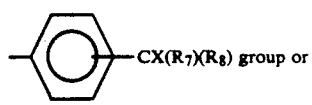

—C(R$_9$)(R$_{10}$)(Z$_3$) group,

X is a chlorine atom or a bromine atom, each of R$_2$, R$_3$, R$_4$, R$_5$, R$_7$, R$_8$, R$_9$, R$_{10}$, Z$_1$, n and m is the same as mentioned above, and each of CX(R$_2$)(R$_3$) group and CX(R$_7$)(R$_8$) group is a meta or para position) is reacted with a hydroperoxide represented by the general formula (II) [and (III)]in the presence of an alkali.

According to a sixth aspect of the invention, there is the provision of a method of producing a dialkyl perox-
ide represented by the general formula (I'), characterized in that an aromatic ketone containing α-hydroperoxy isoalkyl group and represented by the following general formula (VII):

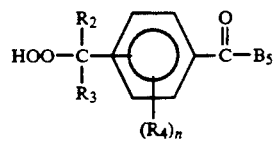

(VIII)

wherein

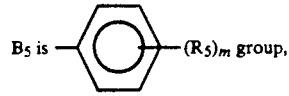

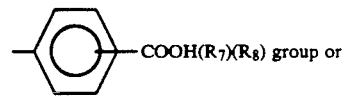

—C(R$_9$)(R$_{10}$)(Z$_2$) group, each of R$_2$, R$_3$, R$_4$, R$_5$, R$_7$, R$_8$, R$_9$, R$_{10}$, Z$_2$, n and m is the same as mentioned above, and each Of COOH(R$_2$)(R$_3$) group and COOH(R$_7$)(R$_8$) group is a metha or para position) is reacted with an alcohol represented by the following general formula (IX) or (X):

R$_1$OH            (IX)

R$_6$OH ...        (X)

(wherein each of R$_1$ and R$_6$ is the same as mentioned above) in the presence of an acid catalyst.

According to a seventh aspect of the invention, there is the provision of a method of producing dialkyl peroxide represented by the general formula (I'), characterized in that an aromatic ketone containing α-hydroperoxy isoalkyl group and represented by the general formula (VII) is reacted with an olefin represented by the following general formula (XI) [and (XII)]:

R$_{13}$R$_{14}$C=CHR$_{15}$...      (XI)

R$_{16}$R$_{17}$C=CHR$_{18}$...      (XII)

(wherein each of R$_{13}$ and R$_{16}$ is an alkyl group having a Carbon number of 1–5 or a phenyl group, each of R$_{14}$ and R$_{17}$ is an alkyl group, and each of R$_{15}$ and R$_{18}$ is a hydrogen atom or a methyl group) in the presence of an acid catalyst.

According to an eighth aspect of the invention, there is the provision of a method of producing a dialkyl peroxide represented by the general formula (I''), characterized in that an aromatic ketone containing α-hydroperoxy isoalkyl group and represented by the following general formula (VII'):

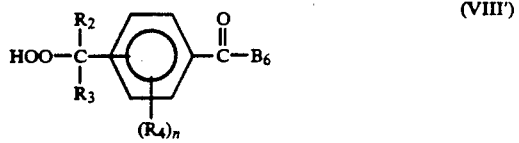

(VIII')

wherein

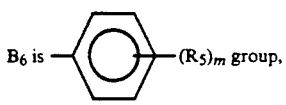

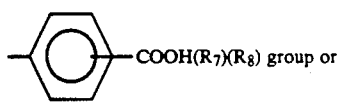

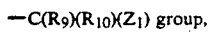

each of $R_2$, $R_3$, $R_4$, $R_5$, $R_7$, $R_8$, $R_9$, $R_{10}$, $Z_1$, m and n is the same as mentioned above, each of $COOH(R_2)(R_3)$ group and $COOH(R_7)(R_8)$ group is a meta or para position) is reacted with a halogenated alkyl represented by the following general formula (XIII) [and (XIV)]:

$$R_1X \ldots \quad (XIII)$$

$$R_6X \ldots \quad (XIV)$$

(wherein each of $R_1$, $R_6$ and X is the same as previously mentioned) in the presence of an alkali.

According to a ninth aspect of the invention, there is the provision of a method of producing a dialkyl peroxide represented by the following genera formula (XVI):

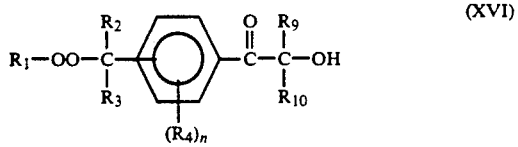

(wherein each of $R_1$, $R_2$, $R_3$, $R_4$, $R_9$, $R_{10}$ and n is the same as previously mentioned, and $R_1OOC(R_2)(R_3)$ group is a metha or para position), characterized in that a compound represented by the following general formula (XV):

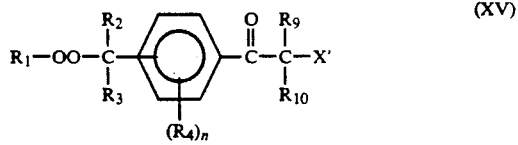

(wherein X' is a halogen atom, each of $R_1$, $R_2$, $R_3$, $R_4$, $R_9$, $R_{10}$ and n is the same as previously mentioned, and $R_1OOC(R_2)(R_3)$ group is a meta or para position) is hydrolyzed in the presence of an alkali.

Tenth and eleventh aspects of the invention lie in a photolysis type radical forming agent and a pyrolysis type radical forming agent using the above novel dialkyl peroxide of the general formula () as an effective ingredient.

The term "photolysis type radical forming agent" used herein means a photopolymerization initiator, a photocuring agent, a photocrosslinking agent or the like, while the term "pyrolysis type radical forming agent" means a polymerization initiator, a crosslinking agent, a curing agent or the like producing radicals through heat.

BRIEF DESCRIPTION OF THE DRAWING

The invention will be described with reference to the accompanying drawing, wherein:

FIG. 1 is a graph showing a relation between irradiation time and degree of conversion in photopolymerization initiators of Examples 83 to 85 according to the invention and Comparative Example 2.

DESCRIPTION OF THE PREFERRED EMBODIMENTS

As a concrete example of the dialkyl peroxides according to the invention, there are mentioned:

(1) 4-(1-t-butylperoxy-1-methylethyl) benzophenone;
(2) 4-(1-t-amylperoxy-1-methylethyl) benzophenone;
(3) 4-(1-t-hexylperoxy-1-methylethyl) benzophenone;
(4) 4-(1-t-octylperoxy-1-methylethyl) benzophenone;
(5) 4-(1-cumylperoxy-1-methylethyl) benzophenone;
(6) 4-(1 t-butylperoxy-1-methylethyl)-2-methyl benzophenone;
(7) 4-(1-t-butylperoxy-1-methylethyl)-2-propyl benzophenone;
(8) 4-(1-t-butylperoxy-1-methylethyl)-2,6-dipropyl benzophenone;
(9) 4-(1-butylperoxy-1-methylethyl)-2,6-dipropyl-4'-t-dodecyl benzophenone;
(10) 4-(1-t-butylperoxy-1-methylethyl)-4'-chloro benzophenone;
(11) 4-(1-t-butylperoxy-1-methylethyl)-4'-bromo benzophenone;
(12) 4-(1-t-butylperoxy-1-methylethyl)-4'-butoxy benzophenone;
(13) 4-(1-t-octylperoxy-1-methylpropyl)-2,6-dipropyl-2',3',4'-trimethoxy benzophenone;
(14) 4-(1-t-octylperoxy-1-methylpropyl)-2,6-dipropyl-3',4'-diethoxy benzophenone;
(15) 3-(1-t-butylperoxy-1-methylethyl) benzophenone;
(16) 3-(1-t-octylperoxy-1-methylpropyl)-6-propyl-3',4'-diethoxy benzophenone;
(17) 4,4'-bis(1-t-butylperoxy-1-methylethyl) benzophenone;
(18) 4,4'-bis(1-t-amylperoxy-1-methylethyl) benzophenone;
(19) 4,4'-bis(1-t-hexylperoxy-1-methylethyl) benzophenone;
(20) 4,4'-bis(1-t-octylperoxy-1-methylethyl) benzophenone;
(21) 4,4'-bis(1-cumylperoxy-1-methylethyl) benzophenone;
(22) 4,4'-bis(1-t-butylperoxy-1-methylethyl)-2-methyl benzophenone;
(23) 4,4'-bis(1-t-butylperoxy-1-methylethyl)-2,6-dimethyl benzophenone;
(24) 4,4'-bis(1-t-octylperoxy-1-methylpropyl)-2,6-diisopropyl benzophenone;
(25) 3,4'-bis(1-t-butylperoxy-1-methylethyl)-6-methyl benzophenone;
(26) 3,4'-bis(1-t-octylperoxy-1-methylethyl)-6-isopropyl benzophenone;
(27) 3,3'-bis(1-t-butylperoxy-1-methylethyl)-6-methyl benzophenone;
(28) 3,3'-bis(1-t-octylperoxy-1-methylethyl)-6-propyl benzophenone;
(29) 1-{4-(1-t-butylperoxyl-methylethyl)phenyl}-2-hydroxy-2-methyl propan-1-one;
(30) 1-{4-(1-t-amylperoxy-1-methylethyl)phenyl}-2-hydroxy-2-methyl propan-1-one;

(31) 1-[4-(1-t-hexylperoxy-1-methylethyl)phenyl]-2-hydroxy-2-methyl propan-1-one:
(32) 1-[4-(1-t-octylperoxy-1-methylethyl)phenyl}-2-hydroxy-2-methyl propan-1-one;
(33) 1-{4-(1-cumylperoxy-1-methylethyl)phenyl]-2-hydroxy-2-methyl propan-1-one;
(34) 1-{4-(1-t-butylperoxy-1-methylethyl)-2,6-dimethylphenyl}-2-hydroxy-2-methyl propan-1-one;
(35) 1{4-(1-t-butylperoxy-1-ethylpropyl)phenyl}-2-hydroxy-2-methyl propan-1-one;
(36) 1-{4-(1-t-butylperoxy-1-methylethyl)phenyl}-2-hydroxy-2-methyl pentan-1-one;
(37) 1-{4-(1-t-butylperoxy-1-methylethyl)phenyl]-2-hydroxy-2-ethyl hexan-1-one;
(38) 1-4-(1-t-butylperoxy-1-methylethyl)benzoyl]-1-hydroxycyclopentane;
(39) 1-{4-(1-t-butylperoxy-1-methylethyl)benzoyl}-1-hydroxy cyclohexane;
(40) 1-{4-(1-t-butylperoxy-1-methylethyl)benzoyl}-1-hydroxy cycloheptane;
(41) 1-{4-(1-t-octylperoxy-1-ethylpropyl)-2,6-diisopropylphenyl}-2-hydroxy-2-butyl h
(42) 1-{4-(1-t-butylperoxy-1-methylethyl)phenyl]-2-chloro-2-methyl propan-1-one;
(43) 1-[4-(1-t-butylperoxy-1-methylethyl)phenyl]-2-bromo-2-methyl propan-1-one;
(44) 1-[4-(1-t-butylperoxy-1-methylethyl)phenyl]-2-methoxy-2-methyl propan-1-one;
(45) 1-{4-(1-t-butylperoxy-1-methylethyl)phenyl}-2-butoxy-2-methyl propan-1-one;
(46) 1-[3-(1-t-butylperoxy-1-methylethyl)phenyl]-2-hydroxy-2-methyl propan-1-one;
(47) 1-[3-(1-t-octylperoxy-1-methylethyl)-6 methylphenyl}-2-hydroxy-2-methyl propan-1-one;
(48) 1-{3-(1-t-hexylperoxy-1-ethylpropyl)-6-methylphenyl]-2-hydroxy-2-methyl propan
(49) 1-[3-(1-t-amylperoxy-1-methylethyl)-6-methylphenyl}-2-chloro-2-methyl propan
(50) 1-{3-(1-cumylperoxy-1-methylethyl)-6-methylphenyl}-2-butoxy-2-methyl propan
(51) 1-{3-(1-t-butylperoxy-1-methylethyl)-6-methylbenzoyl]-1-hydroxy cyclohexane;
(52) 1-{3-(1-t-octylperoxy-1-ethylpropyl)-6-isopropylphenyl]-2-hydroxy-2-butyl hexanlike.

The dialkyl peroxides according to the invention can be produced by the following five methods. In the first production method, the aromatic ketone containing isoalkyl group as shown by the general formula (IV) is reacted with the hydroperoxide of the general formula (II) [and (III)]in the presence of the metal salt to obtain the compound of the general formula (I').

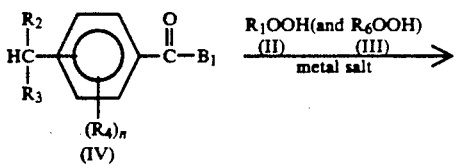

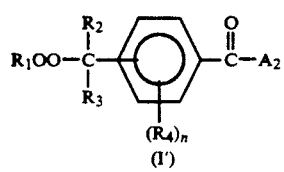

(wherein $R_1$, $R_2$, $R_3$, $R_4$, $R_6$, $B_1$, $A_2$, n and position of $R_1OOC(R_2)(R_3)$ group are the same as previously mentioned).

The starting compound (IV) is easily obtained by Friedel-Crafts reaction of substituted benzene and substituted carboxylic chloride.

In the reaction between the compound (IV) and the hydroperoxide (II) [and (III)], the salt of a metal selected from transition elements of Groups 4 and 5 in the periodic table may be used as a catalyst. As a concrete example of the metal, mention may be made of copper, cobalt, manganese, iron, chromium, zinc and the like, while the ligand therefor includes, for example, a halogen such as iodine, bromine, chlorine; a mineral acid such as sulfuric acid, phosphoric acid, nitric acid, carbonic acid or the like; an organic acid such as formic acid, acetic acid, naphthenic acid, octenoic acid, gluconic acid or the like; cyanogen, acetylacetonate and the like. The amount of the metal salt used is 0 0001-0.1 mol per 1 mol of the hydroperoxide. The reaction conditions are different in accordance with the kind of the metal salt, but the reaction temperature and time are usually 30°-100° C. and 1-50 hours, respectively. Further, benzene, toluene and the like may be used as a solvent. Moreover, it is preferable that oxygen is not existent in the reaction system and the reaction is carried out in an atmosphere of an inert gas such as nitrogen, argon or the like.

In the second production method, the aromatic ketone containing α-hydroxy isoalkyl group (V) is reacted with the hydroperoxide (II) [and (III)]in the presence of an acid catalyst to obtain a compound represented by the general formula (I').

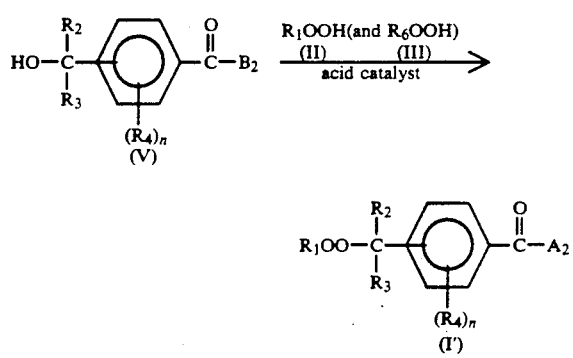

(wherein $R_1$, $R_2$, $R_3$, $R_4$, $R_6$, $B_2$, $A_2$, n and position of $R_1OOC(R_2)(R_3)$ group are the same as previously mentioned).

The starting compound (V) is easily obtained by oxidizing the compound (IV) in air and reducing the resulting hydroperoxide (VII).

In the reaction between the compound (V) and the hydroperoxide (II) [and (III)], a mineral acid such as perchloric acid, hydrochloric acid, sulfuric acid, phosphoric acid or the like is used as an acid catalyst. The amount of the acid catalyst used is 0.001-1 mol per 1 mol of the compound (V). As a solvent, use may be made of acetic acid and the like. Furthermore, the yield can be increased by adding a dehydrating agent such as magnesium sulfate or the like to the reaction system. As the reaction conditions, the reaction temperature is usually 0°-70° C. and the reaction time is preferably 1-10 hours.

Furthermore, the reaction between the hydroperoxide (VII) and alcohol (IX) [and (X)]is carried out in the same manner as mentioned above to obtain a compound represented by the general formula (I').

In the third production method, the aromatic ketone containing isoalkenyl group (VI) is reacted with the hydroperoxide (II) [and (III)]in the presence of the acid catalyst to obtain a compound represented by the general formula (I').

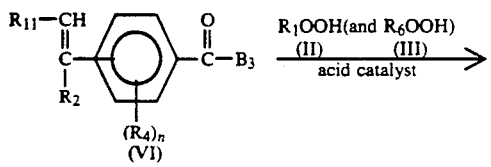

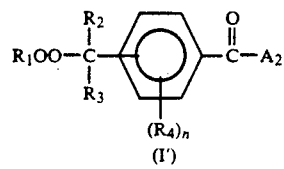

(wherein $R_1$, $R_2$, $R_3$, $R_4$, $R_6$, $R_{11}$, $B_3$, $A_2$, n and position of $R_1OOC(R_2)(R_3)$ group are the same as previously mentioned).

The starting compound (VI) is easily obtained by dehydrating the compound (V).

In the reaction between the compound (VI) and the hydroperoxide (II) [and (III)], a mineral acid such as hydrochloric acid, sulfuric acid, perchloric acid or the like and/or a Lewis acid such as zinc chloride, aluminum chloride or the like is used as an acid catalyst. The amount of the acid catalyst used is 0.001–1 mol per 1 mol of the compound (VI). As the reaction conditions, the reaction temperature is usually 0°–70° C. and the the reaction time is preferably 1–10 hours. Moreover, isopropyl alcohol and the like may be used as a solvent.

Further, the reaction between the hydroperoxide (VII) and the olefin (XI) [and (XII)]is carried out in the same manner as mentioned above to obtain a compound represented by the general formula (I').

In the fourth production method, the aromatic ketone containing α-halogenated isoalkyl group (VII) is reacted with the hydroperoxide (II) [and (III)]in the presence of an alkali to obtain a compound represented by the general formula (I'').

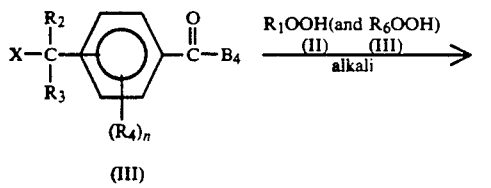

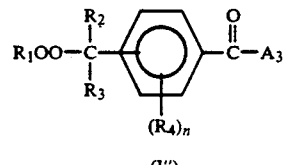

(wherein $R_1$, $R_2$, $R_3$, $R_4$, $R_6$, X, $B_4$, $A_3$, n and position of $R_1OOC(R_2)(R_3)$ group are the same as previously mentioned).

The starting compound (VII) is easily obtained by halogenating the compound (IV) with chlorine gas, N-bromosuccinic imide or the like.

In the reaction between the compound (VII) and the hydroperoxide (II) [and (III)], sodium hydroxide, potassium hydroxide, pyridine and the like may be used as an alkali. The amount of the alkali used is 0.8–3.0 mol per 1 mol of the compound (VII). As the reaction conditions, the reaction temperature is usually 0°–70° C. and the reaction time is preferably 1–10 hours. Moreover, hexane, benzene, toluene, ether and the like may be used as a solvent.

Further, the reaction between the hydroperoxide (VII') and the halogenated alkyl (XIII) [and (XIV)]is carried out in the same manner as mentioned above to obtain a compound represented by the general formula (I').

In the fifth production method, the compound (XV) is hydrolyzed in the presence of an alkali to obtain a compound represented by the general formula (XVI).

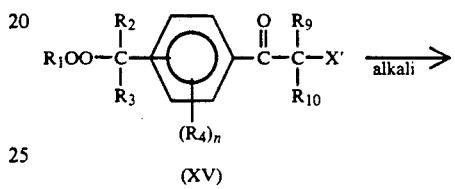

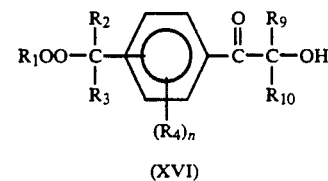

(wherein $R_1$, $R_2$, $R_3$, $R_4$, $R_9$, $R_{10}$, X', n and the position of $R_1OOC(R_2)(R_3)$ group are the same as previously mentioned).

In the hydrolysis of the compound (XV), a hydroxide of an alkali metal such as potassium hydroxide, sodium hydroxide or the like is used as an alkali. This alkali is preferably used as a 1–50% aqueous solution. The amount of the alkali used is 0.1–3.0 mol per 1 mol of the compound (XV). As the reaction conditions, the reaction temperature is usually 0°–70° C. and the reaction time is preferably 1–10 hours. Moreover, ethers, alcohols and the like may be used as a solvent.

The thus obtained dialkyl peroxide can be purified by column chromatography or recrystallization.

The novel dialkyl peroxides obtained according to the invention are white solid or transparent liquid at room temperature. The structure of the dialkyl peroxide can be identified by infrared ray absorption spectrum, nuclear magnetic resonance spectrum, ultraviolet ray absorption spectrum, mass spectrum and elemental analysis.

The dialkyl peroxide according to the invention is used alone or in admixture with another component as a photopolymerization initiator for the photopolymerization or photocuring of radical polymerizable unsaturated compound. In this case, the mixture of one or more radical photopolymerizable unsaturated compound and the photopolymerization initiator according to the invention can be compounded with a proper amount of an additive usually used such as a pigment, a filler, a coloring matter, a thermal polymerization inhibitor, a plasticizer, a solvent, a sensitizer, other known photopolymerization initiator or the like. Such a photosensitive composition is used for paint, adhesive, printing ink, letterpress, printed circuit board, photoresist and the like.

As the radical unsaturated compound to be photopolymerized or photocured through the photopolymerization initiator or photocuring agent according to the invention, mention may be made of polymerizable monomers, polymerizable oligomers and polymerizable unsaturated polymers. The polymerizable monomer is a compound having one or more polymerizable double bond and includes, for example, unsaturated carboxylic acids such as acrylic acid, methacrylic acid, maleic acid, fumaric acid, crotonic acid, itaconic acid and the like; and derivatives of these unsaturated carboxylic acids, for example, monoesters such as methyl(meth)acrylate, butyl(meth)acrylate, 2-ethylhexyl (meth)acrylate, phenyl (meth)acrylate, benzyl (meth)acrylate and the like; hydroxyesters such as 2-hydroxyethyl (meth)acrylate, 2-hydroxypropyl (meth)acrylate and the like; polyvalent esters such as ethyleneglycol di(meth)acrylate, polyethyleneglycol di(meth)acrylate, neopentylglycol di(meth)acrylate, trimethylolpropane tri(meth)acrylate, pentaerythritol tetra(meth)acrylate and the like; (meth)acrylonitrile, (meth)acrylamide and N-substituted (meth)acrylamide; vinyl esters such as vinyl acetate, vinyl propionate, vinyl succinate and the like; vinyl ethers; and vinyl compounds such as styrene, alkylstyrene, halogenated styrene, divinyl benzene, vinyl naphthalene, N-vinylpyrrolidone, diallyl phthalate, diallyl maleate, triallyl isocyanate, triallyl phosphate and the like. As the polymerizable oligomer and polymerizabl unsaturated polymer, mention may be made of setting resins having, for example, maleate group, fumarate group, allyl group or (meth)acrylate group, unsatuerated polyesters, unsaturated acrylic resins, acrylic oligomer modified with isocyanate, polyesteracrylic oligomer, polyether acrylic oligomer and the like.

As a polymer to be crosslinked through the photocrosslinking agent according to the invention, mention may be made of polyethylene, ethylene-propylene copolymer (EPM), ethylene-propylene-diene terpolymer (EPDM), ethylene-vinyl acetate copolymer (EVA), tetrafluoroethylene-vinylidene fluoridehexafluropropylene terpolymer, chlorosulfonated polyethylene, chlorinated polyethylene, polybutene-1, polyisobutene, polybutadiene, polyisoprene, polychloroprene, butadiene-styrene copolymer, natural rubber, polyacrylate rubber, butadiene-acrylonitrile copolymer, acrylonitrile-butadiene-styrene terpolymer, silicone rubber, polyurethane and the like.

The amount of the photopolymerization initiator, photocuring agent or photocrosslinking agent used according to the invention is 0.01-10% by weight, preferably 0.1-4% by weight based on the radical polymerizable unsaturated compound or the polymer to be crosslinked, which is affected by the kind of the additive. For instance, when being mixed with a pigment having a poor light transmission, it may be required to increase the amount used. However, when the amount is too large, the unreacted photopolymerization initiator remains in the resulting polymer and there is a fear of degrading the properties of the polymer. While, when it is too small, the polymerization is not completed and the unreacted unsaturated compound remains.

The photopolymerization, photocuring and photocrosslinking of the radical polymerizable unsaturated compounds using the photopolymerization initiator, photocuring agent or photocrosslinking agent according to the invention is carried out by irradiating a light with a wavelength of 250-500 nm, preferably 300-400 nm according to the well-known method. As a light source, use may be made of daylight, mercury lamp, mercury discharge lamp, xenon arc lamp, flash discharge lamp, tungsten lamp, halogen lamp, coloring laser, excimer laser and the like.

The inventors have made further studies with respect to the use of the dialkyl peroxide according to the invention and found that this peroxide has an effective performance even in the thermal polymerization and thermal crosslinking.

In this case, styrene, α-methylstyrene, acrylonitrile, acrylic esters, methacrylic esters, maleic esters, fumaric esters, maleimides, butadiene, vinyl acetate and the like are used as a vinyl monomer in the thermal polymerization using the initiator according to the invention.

In addition to these monomers, various chain transfer agents, rubber components, or foaming agent such as pentane or the like may be added.

The thermal polymerization initiator according to the invention may be used together with another initiator having a different thermal decomposition temperature.

The amount of the initiator added is different in accordance with the kind of the monomer used in the polymerization or a combination of monomers, but it is generally 0.001-5 parts by weight, preferably 0.01-0.5 part by weight as a pure product per 100 parts by weight of the monomer charged. When the amount is less than 0.001 part by weight, the polymerization speed tends to be slow, while when it exceeds 5 parts by weight, it is uneconomical.

The polymerization method used in the invention is usual block polymerization, solution polymerization or suspension polymerization, wherein the polymerization temperature is usually 60°-150° C., preferably 80°-130° C. The polymerization temperature is constant, or there is adopted a method wherein the polymerization temperature is relatively low at the initial stage and is stepwisely raised with the advance of the polymerization.

As the thus obtained polymer, there are GP type polystyrene used for general shaping material, shock-resistant polystyrene, foamed polystyrene, methyl polymethacrylate, copolymers of various acrylic acids or methacrylic acids such as styrene-acrylonitirle copolymer, styrene-acrylonitrile-phenyl maleimide copolymer, butyl methacrylate-2-ethylhexyl methacrylate copolymer and the like.

As a polymer thermally crosslinked through the dialkyl peroxide according to the invention, mention may be made of polyethylene, ethylene-propylene copolymer (EPM), ethylene-propylene-diene terpolymer (EPDM), ethylene-vinyl acetate copolymer (EVA), tetrafluoroethylene-vinylidene fluoide-hexafluoropropylene terpolymer, chlorosulfonated polyethylene, chlorinated polyethylene, polybutene-1, polyisobutene, polybutadiene, polyisoprene, polychloroprene, butadiene-styrene copolymer, natural rubber, polyacrylate rubber, butadiene-acrylonitrile copolymer, acrylonitrile-butadiene-styrene terpolymer, silicone rubber, polyurethane, polysulfide and the like.

The peroxide according to the invention is added in an amount of 0.1-10% by weight, preferably 1-3% by weight to the polymer to be crosslinked.

Furthermore, various additives generally used in the crosslinking process, such as crosslink assistant, antioxidant, pigment, ultraviolet ray stabilizer, filler, plasticizer and the like may be added to the polymer to be crosslinked.

According to the invention, the temperature for mixing the polymer with the organic peroxide is generally 25°-130° C. The subsequent crosslinking temperature is usually 110°-220° C., preferably 150°-190° C.

The dialkyl peroxides according to the invention have the following characteristics as compared with the conventional photopolymerization initiator.

(1) The dialkyl peroxide according to the invention has a light absorbing group and a radical producing source in the same molecule, so that radicals can efficiently be produced by the irradiation of light. Therefore, the photopolymerization and photocuring rates are fast.

(2) The dialkyl peroxide according to the invention is good in the thermal stability, so that the photopolymerizable composition containing such a peroxide can be stored over a long period without polymerization or gelation.

(3) The resulting polymer is not yellowed when using the dialkyl peroxide according to the invention as a photopolymerization initiator, photocuring agent or photocrosslinking agent.

(4) Since the dialkyl peroxide according to the invention is a peroxide, when the photocuring is insufficient, the post curing through heat is possible.

(5) The dialkyl peroxide according to the invention is also effective as a thermal polymerization initiator or crosslinking agent.

(6) The dialkyl peroxide can efficiently be produced by the method according to the invention.

(7) The dialkyl--. peroxide according to the invention having

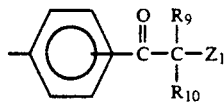

group has two radical producing sources. Therefore, block polymers can be produced by using such a peroxide at a first stage to conduct thermal polymerization and curing and then conducting photopolymerization and curing at a second stage.

(8) When the polymerization is carried ou by using the two-functional dialkyl peroxide according to the invention as an initiator, high molecular weight polymers are obtained. That is, polymers having high strength and improved resistance to solvent and the like can be obtained.

As mentioned above, the dialkyl peroxides according to the invention are novel compounds having improved properties as photopolymerization initiator, photocuring agent, photocrosslinking agent as well as thermal polymerization initiator and thermal crosslinking agent, so that they are very high in the industrial merit.

The following examples are given in illustration of the invention and are not intended as limitations thereof.

EXAMPLE 1

Into a four-necked flask of 200 ml provided with a stirrer and a thermometer was charged a suspension of 11.2 g (0.05 mol) of 4-isopropyl benzophenone (made from cumene and benzoyl chloride), 13.5 g (0.15 mol) of t-butyl hydroperoxide, 0.05 g of cuprous chloride and 50 ml of benzene, which was stirred in a nitrogen gas atmosphere at 70° C. for 25 hours. The resulting product was washed with 10% hydrochloric acid, aqueous solution of 10% sodium hydroxide and water in this order and dried on magnesium sulfate, and after the solvent was removed off, the residue was crystallized in methanol or subjected to a column chromatography to obtain 7.8 g of a white solid. The infrared ray absorption spectrum, nuclear magnetic resonance spectrum, ultraviolet ray absorption spectrum, mass spectrum, elemental analysis and melting point were measured with respect to this compound to obtain the following results, from which the compound was confirmed to be 4-(1-t-butylperoxy-1-methylethyl) benzophenone of

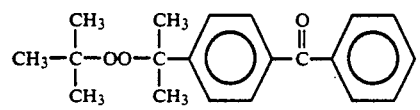

Infrared ray absorption spectrum
  870 cm$^{-1}$ (O—O bond)
  1660 cm$^{-1}$ (C=O bond)
Nuclear magnetic resonance spectrum ($\delta$)
  1.27 ppm (9H)
  1.62 ppm (6H)
  7.4–8.2 ppm (9H)
Ultraviolet ray absorption spectrum (in dioxane)
  342 nm ($\epsilon$160)
  256 nm ($\epsilon$18800)
Mass spectrum
  312 m/e (molecular ion peak)
Elemental analysis C: 76.83% (calculated value 76.89%) H: 7.74% (calculated value 7.74%).
Melting point : 48°–49° C.

EXAMPLES 2-5

The same procedure as in Example 1 was repeated except that t-amyl hydroperoxide, t-hexyl hydroperoxide, t-octyl hydroperoxide and cumene hydroperoxide were used instead of t-butyl hydroperoxide to obtain viscous liquids. These compounds were confirmed to be objective compounds as a result of the same analyses as in Example 1. The obtained compounds and the analytical results thereof are shown in the following Table 1.

TABLE 1

| | Compound | Infrared ray absorption spectrum | Elemental analysis (%) found value (calculated value) | Ultraviolet ray absorption spectrum (in dioxane) | Nuclear magnetic resonance spectrum ($\delta$) | Mass spectrum (m/e) |
|---|---|---|---|---|---|---|
| Example 2 | 4-(1-t-amylperoxy-1-methylethyl)benzophenone | 870 cm$^{-1}$ (O—O bond) 1660 cm$^{-1}$ (C=O bond) | C; 77.15 (77.27) H; 7.98 (8.03) | 265 nm ($\epsilon$ 19200) 342 nm ($\epsilon$ 155) | 0.89 ppm (3H) 1.21 ppm (6H) 1.54 ppm (2H) 1.61 ppm (6H) 7.4–8.4 ppm (9H) | 326 |

TABLE 1-continued

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| Example 3 | 4-(1-t-hexylperoxy-1-methylethyl)benzophenone | 870 cm$^{-1}$ (O—O bond) 1660 cm$^{-1}$ (C=O bond) | C; 77.59 (77.61) H; 8.24 (8.29) | 265 nm (ε 18500) 342 nm (ε 153) | 0.91 ppm (3H) 1.20 ppm (6H) 1.54 ppm (4H) 1.61 ppm (6H) 7.4–8.4 ppm (9H) | 340 |
| Example 4 | 4-(1-t-octylperoxy-1-methylethyl)benzophenone | 870 cm$^{-1}$ (O—O bond) 1660 cm$^{-1}$ (C=O bond) | C; 78.22 (78.22) H; 8.72 (8.75) | 265 nm (ε 18700) 342 nm (ε 160) | 1.03 ppm (9H) 1.20 ppm (6H) 1.57 ppm (2H) 1.60 ppm (6H) 7.3–8.2 ppm (9H) | 368 |
| Example 5 | 4-(1-cumylperoxy-1-methylethyl)benzophenone | 870 cm$^{-1}$ (O—O bond) 1660 cm$^{-1}$ (C=O bond) | C; 80.13 (80.18) H; 6.96 (7.00) | 265 nm (ε 22000) 342 nm (ε 178) | 1.60 ppm (12H) 7.2–8.6 ppm (14H) | 374 |

EXAMPLES 6–9

The same procedure as in Example 1 was repeated except that various substituted 4-isopropyl benzophenones were used instead of 4-isopropyl benzophenone and the same analyses as in Example 1 were conducted, from which the resulting compounds were confirmed to be objective compounds. These compounds and the analytical results thereof are shown in the following Table 2.

EXAMPLES 10–14

The same procedure as in Example 1 was repeated except that various substituted 3-isopropyl benzophenones were used instead of 4-isopropyl benzophenone and the same analyses as in Example 1 were conducted, from which the resulting products were confirmed to be objective compounds. The compounds and the analytical results thereof are shown in the following Table 3.

TABLE 2

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| Example 6 | 4-(1-t-butylperoxy-1-methylethyl)-2-methyl benzophenone | 870 cm$^{-1}$ (O—O bond) 1660 cm$^{-1}$ (C=O bond) | C; 77.22 (77.27) H; 7.99 (8.03) | 263 nm (ε 19100) 342 nm (ε 230) | 1.26 ppm (9H) 1.62 ppm (6H) 2.40 ppm (3H) 7.4–8.2 ppm (8H) | 326 |
| Example 7 | 4-(1-t-butylperoxy-1-methylethyl)-4'-dodecyl benzophenone | 870 cm$^{-1}$ (O—O bond) 1660 cm$^{-1}$ (C=O bond) | C; 79.89 (79.95) H; 10.05 (10.06) | 264 nm (ε 25000) 342 nm (ε 240) | 0.91 ppm (3H) 1.30 ppm (29H) 1.64 ppm (6H) 2.60 ppm (2H) 7.2–8.3 ppm (8H) | 480 |
| Example 8 | 4-(1-t-butylperoxy-1-methylethyl)2',4'-dichloro benzophenone | 870 cm$^{-1}$ (O—O bond) 1670 cm$^{-1}$ (C=O bond) | C; 62.24 (63.00) H; 5.77 (5.82) Cl; 18.51 (18.59) | 261 nm (ε 32000) 344 nm (ε 190) | 1.27 ppm (9H) 1.64 ppm (6H) 7.2–8.4 ppm (4H) | 381 |
| Example 9 | 4-(1-t-butylperoxy-1-methylethyl)-4'-butoxy benzophenone | 870 cm$^{-1}$ (O—O bond) 1670 cm$^{-1}$ (C=O bond) | C; 79.90 (79.95) H; 8.38 (8.39) | 282 nm (ε 21000) 330 nm (ε 450) | 0.98 ppm (3H) 1.1–2.3 ppm (19H) 3.93 ppm (2H) 7.2–8.4 ppm (14H) | 384 |

TABLE 3

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| Example 10 | 3-(1-t-butylperoxy-1-methylethyl)benzophenone | 870 cm$^{-1}$ (O—O bond) 1660 cm$^{-1}$ (C=O bond) | C; 76.83 (76.89) H; 7.73 (7.74) | 258 nm (ε 17000) 342 nm (ε 148) | 1.26 ppm (9H) 1.63 ppm (6H) 7.1–8.1 ppm (9H) | 312 |
| Example 11 | 3-(1-t-butylperoxy-1-methylethyl)-6-methyl benzophenone | 870 cm$^{-1}$ (O—O bond) 1660 cm$^{-1}$ (C=O bond) | C; 77.28 (77.27) H; 8.00 (8.03) | 264 nm (ε 18100) 342 nm (ε 210) | 1.26 ppm (9H) 1.62 ppm (6H) 2.40 ppm (3H) 7.2–8.2 ppm (8H) | 326 |
| Example 12 | 3-(1-t-butylperoxy-1-methylethyl)-4'-methyl benzophenone | 870 cm$^{-1}$ (O—O bond) 1660 cm$^{-1}$ (C=O bond) | C; 77.25 (77.27) H; 7.98 (8.03) | 265 nm (ε 18000) 342 nm (ε 205) | 1.26 ppm (9H) 1.63 ppm (6H) 2.34 ppm (3H) 7.2–8.3 ppm (8H) | 326 |
| Example 13 | 3-(1-t-butylperoxy-1-methylethyl)-4'-chloro benzophenone | 870 cm$^{-1}$ (O—O bond) 1670 cm$^{-1}$ (C=O bond) | C; 69.19 (69.26) H; 6.62 (6.68) Cl; 10.11 (10.22) | 260 nm (ε 25500) 344 nm (ε 170) | 1.26 ppm (9H) 1.63 ppm (6H) 7.1–8.3 ppm (8H) | 346 |
| Example 14 | 3-(1-t-butylperoxy-1-methylethyl)-2',3',4'-triethoxy benzophenone | 870 cm$^{-1}$ (O—O bond) 1670 cm$^{-1}$ (C=O bond) | C; 70.69 (70.72) H; 8.31 (8.35) | 280 nm (ε 22300) 328 nm (ε 510) | 1.2–1.6 ppm (18H) 1.64 ppm (6H) 2.44 ppm (3H) | 458 |

TABLE 3-continued

| Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|
| | | | | 3.7–4.3 ppm (6H) 7.1–8.1 ppm (5H) | |

EXAMPLE 15

Into a four-necked flask of 100 ml provided with a stirrer and a thermometer was charged a suspension of 12.0 g (0.05 mol) of 4-(α-hydroxyisopropyl) benzophenone, 5.0 g (0.05 mol) of t-butyl hydroperoxide and 0.2 g of magnesium sulfate, to which was added dropwise 5.0 g (0.0005 mol) of 1% perchloric acid in acetic acid while maintaining temperature below 25° C. The resulting mixture was stirred for 2 hours after the temperature was raised to 40° C. After the cooling, the resulting product was washed with an aqueous solution of 5% sodium hydroxide and further with water, dried on anhydrous magnesium sulfate and after the solvent was removed off, the residue was crystallized in methanol or subjected to column chromatography to obtain 11.8 g of a white solid. As a result of the same analyses as in Example 1, the thus obtained compound was confirmed to be 4-(1-t-butylperoxy-1-methylethyl) benzophenone.

EXAMPLE 16

Into a four-necked flask of 100 ml provided with a stirrer and a thermometer was charged a solution of 11.1 g (0.05 mol) of 4-isopropenyl benzophenone in 35 isopropyl alcohol, to which were added dropwise 1.0 g (0.01 mol) of concentrated hydrochloric acid and further 5.0 g (0.055 mol) of t-butyl hydroperoxide while maintaining temperature below 25° C. The resul ing mixture was stirred for 2 hours after the temperature was raised to 40° C. After the cooling, the resulting product was washed with an aqueous solution of 5% sodium hydroxide and further with water, dried on magnesium sulfate and after the solvent was removed off, the residue was crystallized in methanol or subjected to column chromatography to obtain 10.7 g of a white solid. As a result of the same analyses as in Example 1, the thus obtained compound was confirmed to be 4-(1-t-butylperoxy-1-methylethyl) benzophenone.

EXAMPLE 17

Into a four-necked flask of 200 ml provided with a stirrer and a thermometer were charged 12.5 g (0.125 mol) of an aqueous solution of 40% sodium hydroxide, 25 g of benzene and 75 g of dioxane with stirring, to which were added 1.3 g (0.125 mol) of t-butyl hydroperoxide and 25.9 g (0.10 mol) of 4-(α-chloroi benzophenone while cooling on ice at 3°–6° C. Thereafter, the resulting mixture was stirred at 5° C. for 4–5 hours. Then, the organic phase was taken out from the reaction mixture, washed with 10% sodium hydroxide 2 times and with saturated saline water 2 to 3 times, dried on anhydrous magnesium sulfate, and after the solvent was removed off, the residue was crystallized in methanol or subjected to column chromatography to obtain 22.1 g of a white solid. As a result of the same analyses as in Example 1, the resulting compound was confirmed to be 4-(1-t-butylperoxy-1-methylethyl) benzophenone.

EXAMPLE 18

The same procedure as in Example 15 was repeated except that t-butyl alcohol and 4-(α-hydroperoxyisopropyl) benzophenone were used instead of 4-(α-hydroxyisopropyl) benzophenone and t-butyl hydroperoxide and the same analyses as in Example 1 were conducted, from which the resulting compound was confirmed to be 4-(1-t-butylperoxy-1-methylethyl) benzophenone.

EXAMPLE 19

The same procedure as in Example 16 was repeated except that 2-methyl-1-pentene and 4-(α-hydroperoxyisopropyl) benzophenone were used instead of 4-isopropenyl benzophenone and t-butyl hydroperoxide and the same analyses as in Example 1 were conducted, from which the resulting compound was confirmed to be 4-(1-t-hexylperoxy-1-methylethyl) benzophenone.

EXAMPLE 20

The same procedure as in Example 17 was repeated except that t-butyl chloride and 4-(α-hydroperoxyisopropyl) benzophenone were used instead of 4-(α-chloroisopropyl) benzophenone and t-butyl hydroperoxide and the same analyses as in Example 1 were conducted, from which the resulting compound was confirmed to be 4-(1-t-butylperoxy-1-methylethyl) benzophenone.

EXAMPLE 21

Into a four-necked flask of 200 ml provided with a stirrer and a thermometer was charged a suspension of 13.3 g (0.05 mol) of 4,4'-diisopropyl benzophenone (obtained by reacting cumene and cumaric acid chloride in the presence of aluminum chloride), 27.0 g (0.3 mol) of t-butyl hydroperoxide, 0.1 g of cuprous chloride and 50 ml of benzene, and stirred in a nitrogen gas atmosphere at 70° C. for 25 hours. The reaction mixture was washed with 10% hydrochloric acid, aqueous solution of 10% sodium hydroxide and water in this order, dried on magnesium sulfate, and after the solvent was removed off, the residue was crystallized in methanol or subjected to column chromatography to obtain 5.3g of a white solid. The infrared ray absorption spectrum, nuclear magnetic resonance spectrum, ultraviolet ray absorption spectrum, mass spectrum, elemental analysis and melting point were measured with respect to this compound to obtain the following results, from which the compound was confirmed to be 4,4'-bis(1-t-butylperoxy-1-methylethyl) benzophenone of

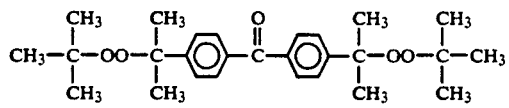

Infrared ray absorption spectrum 870 cm$^{-1}$ (O—O bond)
1660 cm$^{-1}$ (C=O bond)

lytical results thereof are shown in the following Table 4.

TABLE 4

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| Example 22 | 4,4'-bis(1-t-amylperoxy-1-methylethyl) benzophenone | 870 cm$^{-1}$ (O—O bond) 1660 cm$^{-1}$ (C=O bond) | C; 73.98 (74.01) H; 8.99 (9.00) | 261 nm (ε 22500) 342 nm (ε 190) | 0.90 ppm (6H) 1.21 ppm (12H) 1.54 ppm (4H) 1.61 ppm (12H) 7.4–8.1 ppm (8H) | 470 |
| Example 23 | 4,4'-bis(1-t-hexylperoxy-1-methylethyl) benzophenone | 870 cm$^{-1}$ (O—O bond) 1660 cm$^{-1}$ (C=O bond) | C; 74.66 (74.66) H; 9.26 (9.30) | 262 nm (ε 22300) 342 nm (ε 195) | 0.90 ppm (6H) 1.20 ppm (12H) 1.54 ppm (8H) 1.60 ppm (12H) 7.4–8.1 ppm (8H) | 498 |
| Example 24 | 4,4'-bis(1-t-octylperoxy-1-methylethyl) benzophenone | 870 cm$^{-1}$ (O—O bond) 1660 cm$^{-1}$ (C=O bond) | C; 75.73 (75.77) H; 9.80 (9.81) | 261 nm (ε 23000) 342 nm (ε 200) | 1.05 ppm (18H) 1.20 ppm (12H) 1.58 ppm (6H) 1.62 ppm (12H) 7.3–8.2 ppm (8H) | 554 |
| Example 25 | 4,4'-bis-(1-cumylperoxy-1-methylethyl) benzophenone | 870 cm$^{-1}$ (O—O bond) 1660 cm$^{-1}$ (C=O bond) | C; 78.35 (78.41) H; 7.43 (7.47) | 259 nm (ε 27000) 342 nm (ε 222) | 1.61 ppm (24H) 7.2–8.3 ppm (18H) | 556 |

Nuclear magnetic resonance spectrum (δ)
1.27 ppm (18H)
1.60 ppm (12H)
7.5–7.9 ppm (8H)
Ultraviolet ray absorption spectrum (in dioxane)
261 nm (ε22000)
342 nm (ε196)
Mass spectrum
442 m/e (molecular ion peak)
Elemental analysis.
C: 73.21% (calculated value 73.27%).,
H: 8.63% (calculated value 8.65%)
Melting point: 88°–89° C.

EXAMPLES 22–25

The same procedure as in Example 21 was repeated except that t-amyl hydroperoxide, t-hexyl hydroperoxide, t-octyl hydroperoxide and cumene hydroperoxide were used instead of t-butyl hydroperoxide to obtain viscous liquids. These compounds were confirmed to be objective compounds as a result of the same analyses as in Example 21. The obtained compounds and the ana-

EXAMPLES 26–29

The same procedure as in Example 21 was repeated except that various diisopropyl benzophenones were used instead of 4,4'-diisopropyl benzophenone and the same analyses as in Example 21 were conducted, from which the resulting compounds were confirmed to be objective compounds. These compounds and the analytical results thereof are shown in the following Table 5.

TABLE 5

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| Example 26 | 4,4'-bis(1-t-butylperoxy-1-methylethyl)-2-methyl benzophenone | 870 cm$^{-1}$ (O—O bond) 1660 cm$^{-1}$ (C=O bond) | C; 73.63 (73.65) H; 8.80 (8.83) | 259 nm (ε 23000) 342 nm (ε 238) | 1.26 ppm (18H) 1.61 ppm (12H) 2.40 ppm (3H) 7.4–8.1 ppm (7H) | 456 |
| Example 27 | 3,4'-bis(1-t-butylperoxy-1-methylethyl) benzophenone | 870 cm$^{-1}$ (O—O bond) 1660 cm$^{-1}$ (C=O bond) | C; 73.22 (73.27) H; 8.65 (8.65) | 262 nm (ε 20000) 342 nm (ε 175) | 1.27 ppm (18H) 1.62 ppm (12H) 7.4–8.0 ppm (8H) | 442 |
| Example 28 | 3,3'-bis(1-t-butylperoxy-1-methylethyl)-6-methyl benzophenone | 870 cm$^{-1}$ (O—O bond) 1660 cm$^{-1}$ (C=O bond) | C; 73.62 (73.65) H; 8.81 (8.83) | 264 nm (ε 19900) 342 nm (ε 170) | 1.26 ppm (18H) 1.61 ppm (12H) 2.38 ppm (3H) 7.4–8.2 ppm (7H) | 456 |
| Example 29 | 4,4'-bis(1-t-butylperoxy-1-methylethyl)-2,6-diisopropyl benzophenone | 870 cm$^{-1}$ (O—O bond) 1660 cm$^{-1}$ (C=O bond) | C; 75.22 (75.25) H; 9.55 (9.57) | 257 nm (ε 24500) 342 nm (ε 256) | 1.20 ppm (12H) 1.27 ppm (18H) 1.61 ppm (12H) 3.12 ppm (2H) 7.2–8.0 ppm (6H) | 526 |

EXAMPLE 30

Into a four-necked flask of 100 ml provided with a stirrer and a thermometer was charged a suspension of 14.9 g (0.05 mol) of 4,4'-bis(α-hydroxyisopropyl) benzophenone, 10.0 g (0.11 mol) of t-butyl hydroperoxide and 4.0 g of magnesium sulfate, to which was added dropwise 10.0 g (0.001 mol) of a solution of 1% perchloric acid in acetic acid while maintaining temperature below 25° C., and then the stirring was continued for 2 hours after the temperature was raised to 40° C. After the cooling, the reaction mixture was washed with an aqueous solution of 5% sodium hydroxide and further with water, dried on anhydrous magnesium sulfate, and after the solvent was removed off, the residue was crystallized in methanol or subjected to column chromatography to obtain 15.2 g of a white solid. As a result of the same analyses as in Example 21, the resulting compound was confirmed to be 4,4'-bis(1-t-butylperoxy-1-methylethyl) benzophenone.

EXAMPLE 31

Into a four-necked flask of 100 ml provided with a stirrer and a thermometer was charged a solution of 13.1 g (0.05 mol) of 4,4'-diisopropenyl benzophenone in isopropyl alcohol, to which were added dropwise 2.0 g (0.02 mol) of concentrated hydrochloric acid and further 10.0 g (0.11 mol) of t-butyl hydroperoxide while maintaining temperature below 25° C., and then the stirring was continued for 2 hours after the temperature was raised to 40° C. After the cooling, the reaction mixture was washed with an aqueous solution of 5% sodium hydroxide and further with water, dried on magnesium sulfate, and after the solvent was removed off, the residue was crystallized in methanol or subjected to column chromatography to obtain 14.2 g of a white solid. As a result of the same analyses as in Example 21, the resulting compound was confirmed to be 4,4'-bis(1-t-butylperoxy-1-methylethyl) benzophenone.

EXAMPLE 32

Into a four-necked flask of 200 ml provided with a stirrer and a thermometer were charged 25.0 g (0.25 mol) of an aqueous solution of 40% sodium hydroxide, 25 g of benzene and 75 g of dioxane with stirring, to which added 22.6 g (0.25 mol) of t-butyl hydroperoxide and 33.5 g of 4,4'-bis(α-chloroisopropyl) benzophenone while cooling on ice at 3°-6° C. Thereafter, the reaction was continued at 5° C. for 4–5 hours. The organic phase was taken out from the reaction mixture, washed with 10% sodium hydroxide 2 times and with saturated saline water 2 to 3 times, dried on anhydrous magnesium sulfate, and after the solvent was removed off, the residue was crystallized in methanol or subjected to column chromatography to obtain 32.4 g of a white solid. As a result of the same analyses as in Example 21, the resulting compound was confirmed to be 4,4'- bis(1-t-butylperoxy-1-methylethyl) benzophenone.

EXAMPLE 33

The same procedure as in Example 30 was repeated except that t-butyl alcohol and 4,4'-bis(α-hydroperoxyisopropyl) benzophenone were used instead of 4,4'-bis-(α-hydroxyisopropyl) benzophenone and t-butyl hydroperoxide, and the same analyses as in Example 21 were conducted, from which the resulting compound was confirmed to be 4,4'-bis(1-t-butylperoxy-1-methylethyl) benzophenone.

EXAMPLE 34

The same procedure as in Example 31 was repeated 2-methyl-1-pentene and 4,4'-bis(α-hydroperoxyisopropyl) benzophenone were used instead of 4,4'-diisopropenyl benzophenone and t-butyl hydroperoxide, and the same analyses as in Example 21 were conducted, from which the resulting compound was confirmed to be 4,4'-bis(1-t-hexylperoxy-1-methylethyl) benzophenone.

EXAMPLE 35

The same procedure as in Example 32 was repeated except that t-butyl chloride and 4,4'-bis(α-hydroperoxyisopropyl) benzophenone were used instead of 4,4'-bis-(α-chloroisopropyl) benzophenone and t-butyl hydroperoxide, and the same analyses as in Example 21 were conducted, from which the resulting compound was confirmed to be 4,4'-bis(1-t-butylperoxy-1-methylethyl) benzophenone.

EXAMPLE 36

Into a four-necked flask of 100 ml provided with a stirrer and a thermometer was charged a suspension of 14.9 g (0.05 mol) of 4,4'-bis(α-hydroxyisopropyl) benzophenone, 4.5 g of t-butyl hydroperoxide and 4.0 g of magnesium sulfate, to which was added dropwise 10.0 g (0.001 mol) of a solution of 1% perchloric acid in acetic acid while maintaining temperature below 25° C. and the stirring was continued for 4 hours. Then, 5.2 g (0.05 mol) of t-amyl hydroperoxide was added dropwise and the stirring was further continued for 4 hours. After the cooling, the reaction mixture was washed with an aqueous solution of 5% sodium hydroxide and further with water, dried on anhydrous magnesium sulfate, and after the solvent was removed off, the residue was subjected to column chromatography to obtain 11.4 g of a white solid. The same analyses as in Example 21 were conducted to obtain results a shown in the following Table 6, from which the resulting compound was confirmed to be 4-(1-t-butylperoxy-1-methylethyl)-4'-(1-t-amylperoxy-1-methylethyl) benzophenone.

EXAMPLES 37–38

The same procedure as in Example 36 was repeated except that various hydroperoxides were used instead of t-butyl hydroperoxide and t-amyl hydroperoxide, and the same analyses as in Example 21 were conducted, from which the resulting compounds were confirmed to be objective peroxides. The obtained compounds and the analytical results thereof are also shown in Table 6.

TABLE 6

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| Example 36 | 4-(1-t-butylperoxy-1-methylethyl)-4'-(1-t-amylperoxy-1-methylethyl) benzophenone | 870 cm$^{-1}$ (O—O bond) 1660 cm$^{-1}$ (C=O bond) | C; 73.62 (73.65) H; 8.79 (8.83) | 261 nm (ε 22200) 342 nm (ε 195) | 0.90 ppm (3H) 1.21 ppm (6H) 1.27 ppm (9H) 1.54 ppm (2H) 1.61 ppm (12H) 7.4–8.0 ppm (8H) | 456 |
| Example 37 | 4-(1-t-hexylperoxy-1-methylethyl)-4'-(1-t-octylperoxy-1- | 870 cm$^{-1}$ (O—O bond) 1660 cm$^{-1}$ (C=O bond) | C; 75.24 (75.25) H; 9.54 (9.57) | 261 nm (ε 23000) 342 nm (ε 199) | 0.90 ppm (3H) 1.04 ppm (9H) 1.55 ppm (6H) | 526 |

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| | methylethyl)benzophenone | | | | 1.60 ppm (12H) 7.4–8.1 ppm (8H) | |
| Example 38 | 4-(1-t-butylperoxy-1-methylethyl)-4'-(1-cumylperoxy-1-methylethyl)benzophenone | 870 cm$^{-1}$ (O—O bond) 1660 cm$^{-1}$ (C=O bond) | C; 76.12 (76.16) H; 7.96 (7.99) | 261 nm (ε 25000) 342 nm (ε 210) | 1.26 ppm (9H) 1.60 ppm (18H) 7.2–8.3 ppm (13H) | 504 |

EXAMPLE 39

Into a four-necked flask of 200 ml provided with a stirrer and a thermometer was charged a suspension of 13.5 g (0.05 mol) of p-isopropyl-α-bromoisobutyro phenone (made from cumene and α-bromoisobutyryl chloride), 13.5 g (0.15 mol) of t-butyl hydroperoxide, 0.05 g of cuprous chloride and 50 ml of benzene, which was stirred in a nitrogen gas atmosphere at 70° C. for 25 hours. Then, the reaction mixture was washed with 10% hydrochloric acid, aqueous solution of 10% sodium hydroxide and water in this order, dried on magnesium sulfate, and after the solvent was removed off, the residue was subjected to column chromatography to obtain 8.5 g of a white solid. The infrared ray absorption spectrum, nuclear magnetic resonance spectrum, ultraviolet ray absorption spectrum, mass spectrum, elemental analysis and melting point were measured with respect to this compound to obtain the following results, from which the compound was confirmed to be 1-{4-(1-t-butylperoxy-1-methylethyl) phenyl]-2-bromo-2-methyl propan-1-one of

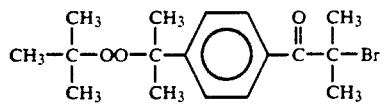

Infrared ray absorption spectrum 870 cm$^{-1}$ (O—O bond)
1675 cm$^{-1}$ (C=O bond)

Nuclear magnetic resonance spectrum (δ)
 1.24 ppm (9H)
 1.59 ppm (6H)
 2.01 ppm (6H)
 7.4–8.2 ppm (4H)

Ultraviolet ray absorption spectrum (in dioxane)
 265 nm (ε15000)
 329 nm (ε205)

Mass spectrum
 357 m/e (molecular ion peak)

Elemental analysis. C: 57.13% (calculated value 57.15%), H: 7.01% (calculated value 7.05%)., Br: 22.31% (calculated value 22.36).

Melting point: 73° C.

EXAMPLES 40–43

The same procedure as in Example 39 was repeated except that t-amyl hydroperoxide, t-hexyl hydroperoxide, t-octyl hydroperoxide and cumene hydroperoxide were used instead of t-butyl hydroperoxide to obtain viscous liquids. These compounds were confirmed to be objective compounds as a result of the same analyses as in Example 39. The obtained compounds and the analytical results thereof are shown in the following Table 7.

TABLE 7

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| Example 40 | 1-{4-(1-t-amylperoxy-1-methylethyl)phenyl}-2-bromo-2-methyl propan-1-one | 870 cm$^{-1}$ (O—O bond) 1675 cm$^{-1}$ (C=O bond) | C; 58.20 (58.23) H; 7.31 (7.33) Br; 21.50 (21.52) | 263 nm (ε 15500) 328 nm (ε 210) | 0.89 ppm (3H) 1.20 ppm (6H) 1.52 ppm (2H) 1.60 ppm (6H) 2.02 ppm (6H) 7.4–8.4 ppm (4H) | 371 |
| Example 41 | 1-{4-(1-t-hexylperoxy-1-methylethyl)phenyl}-2-bromo-2-methyl propan-1-one | 870 cm$^{-1}$ (O—O bond) 1675 cm$^{-1}$ (C=O bond) | C; 59.20 (59.22) H; 7.59 (7.59) Br; 20.70 (20.74) | 263 nm (ε 16200) 329 nm (ε 200) | 0.90 ppm (3H) 1.22 ppm (6H) 1.53 ppm (4H) 1.60 ppm (6H) 2.00 ppm (6H) 7.4–8.4 ppm (4H) | 385 |
| Example 42 | 1-{4-(1-t-octylperoxy-1-methylethyl)phenyl}-2-bromo-2-methyl propan-1-one | 870 cm$^{-1}$ (O—O bond) 1675 cm$^{-1}$ (C=O bond) | C; 60.96 (61.01) H; 8.06 (8.05) Br; 19.29 (19.33) | 264 nm (ε 16100) 329 nm (ε 202) | 1.01 ppm (9H) 1.20 ppm (6H) 1.56 ppm (2H) 1.62 ppm (6H) 2.02 ppm (6H) 7.3–8.2 ppm (4H) | 413 |
| Example 43 | 1-{4-(1-cumylperoxy-1-methylethyl)phenyl}-2-bromo-2-methyl propan-1-one | 870 cm$^{-1}$ (O—O bond) 1675 cm$^{-1}$ (C=O bond) | C; 63.00 (63.01) H; 6.46 (6.49) Br; 19.01 (19.05) | 260 nm (ε 17100) 330 nm (ε 215) | 1.60 ppm (12H) 2.00 ppm (6H) 7.2–8.6 ppm (9H) | 419 |

EXAMPLES 44-48

The same procedure as in Example 39 was repeated except that various aromatic ketones containing isopropyl group were used instead of p-isopropyl-α-bromoisobutyro phenone and the same analyses as in Example 39 were conducted, from which the resulting compounds were confirmed to be objective compounds. These compounds and the analytical results thereof are shown in the following Table 8.

Infrared ray absorption spectrum
  870 cm$^{-1}$ (O—O bond)
  1665 cm$^{-1}$ (C=O bond)
  3450 cm$^{-1}$ (O-H bond)
Nuclear magnetic resonance spectrum (δ)
  1.24 ppm (9H)
  1.57 ppm (6H)
  1.65 ppm (6H)
  4.21 ppm (1H)
  7.5-8.2 ppm (4H)

TABLE 8

| | Compound | Infrared ray absorption spectrum | Elemental analysis (%) found value (calculated value) | Ultraviolet ray absorption spectrum (in dioxane) | Nuclear magnetic resonance spectrum (δ) | Mass spectrum (m/e) |
|---|---|---|---|---|---|---|
| Example 44 | 1-{4-(1-t-butylperoxy-1-methylethyl)phenyl}-2-methoxy-2-methyl propan-1-one | 870 cm$^{-1}$ (O—O bond)<br>1675 cm$^{-1}$ (C=O bond) | C; 70.06 (70.10)<br>H; 9.13 (9.15) | 269 nm (ε 18000)<br>333 nm (ε 240) | 1.25 ppm (9H)<br>1.55 ppm (6H)<br>1.60 ppm (6H)<br>3.21 ppm (3H)<br>7.4-8.4 ppm (4H) | 308 |
| Example 45 | 1-{4-(1-t-butylperoxy-1-methylethyl)phenyl}-2-butoxy-2-methyl propan-1-one | 870 cm$^{-1}$ (O—O bond)<br>1675 cm$^{-1}$ (C=O bond) | C; 71.95 (71.96)<br>H; 9.79 (9.78) | 270 nm (ε 18400)<br>332 nm (ε 250) | 0.91 ppm (3H)<br>1.1-1.4 ppm (13H)<br>1.54 ppm (6H)<br>1.61 ppm (6H)<br>3.40 ppm (2H)<br>7.4-8.4 ppm (4H) | 350 |
| Example 46 | 1-{4-(1-t-butylperoxy-1-methylethyl)-2,6-diisopropyl phenyl}-2-chloro-2-methyl propan-1-one | 870 cm$^{-1}$ (O—O bond)<br>1675 cm$^{-1}$ (C=O bond) | C; 69.55 (69.59)<br>H; 9.37 (9.39)<br>Cl; 8.90 (8.93) | 267 nm (ε 17600)<br>329 nm (ε 213) | 1.15 ppm (12H)<br>1.21 ppm (9H)<br>1.60 ppm (6H)<br>1.82 ppm (6H)<br>3.08 ppm (2H)<br>7.6 ppm (2H) | 397 |
| Example 47 | 1-{3-(1-t-butylperoxy-1-methylethyl)-6-methyl phenyl}-2-chloro-2-methyl propan-1-one | 870 cm$^{-1}$ (O—O bond)<br>1670 cm$^{-1}$ (C=O bond) | C; 66.12 (66.14)<br>H; 8.31 (8.33)<br>Cl; 10.81 (10.85) | 264 nm (ε 15400)<br>327 nm (ε 184) | 1.21 ppm (9H)<br>1.58 ppm (6H)<br>1.80 ppm (6H)<br>2.43 ppm (3H)<br>2.43 ppm (3H)<br>7.4-8.2 ppm (3H) | 326 |
| Example 48 | 1-{4-(1-t-butylperoxy-1-methylethyl)benzoyl}-1-chloro cyclohexane | 870 cm$^{-1}$ (O—O bond)<br>1670 cm$^{-1}$ (C=O bond) | C; 68.04 (68.07)<br>H; 8.27 (8.28)<br>Cl; 10.00 (10.05) | 265 nm (ε 16200)<br>329 nm (ε 220) | 1.20 ppm (9H)<br>1.2-1.7 ppm (12H)<br>2.00 ppm (4H)<br>7.4-8.2 ppm (4H) | 352 |

EXAMPLE 49

A mixed solution of 3.6 g (0.01 mol) of 1-(4-(1-t-butyl-peroxy-1-methylethyl) phenyl}-2-bromo-2-methyl propan-1-one obtained in Example 39, 30 ml of aqueous solution of 20% sodium hydroxide and 50 ml of isopropyl alcohol was stirred at 60° C. for 1 hour. After the cooling, the reaction mixture was added with 50 ml of hexane, washed with saturated saline water and with water, dried on magnesium sulfate, and after the solvent was removed off, the residue was subjected to column chromatography to obtain 2.4 g of a white solid. The same analyses as in Example 39 were conducted to obtain results as mentioned below, from which the resulting compound was confirmed to be 1-{4-(1-t-butyl-peroxy-1-methylethyl) phenyl}-2-hydroxy-2-methyl propan-1-one of

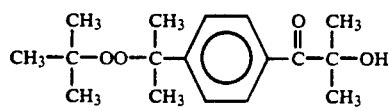

Ultraviolet ray absorption spectrum (in dioxane)
  256 nm (ε16000)
  327 nm (ε109)
Mass spectrum
  294 m/e (molecular ion peak)
Elemental analysis: C: 69.33% (calculated value 69.36%), H: 8.89% (calculated value 8.90%)
Melting point: 66° C.

EXAMPLES 50-56

The same procedure as in Example 49 was repeated except that various compounds obtained in Examples 40-43 and 46-48 were used instead of 1-{4-(1-t-butyl-peroxy-1-methylethyl) phenyl]-2-bromo-2-methyl propan-1-one, and the same analyses as in Example 39 were conducted, from which the resulting compounds were confirmed to be objective compounds. These compounds and the analytical results thereof are shown in the following Table 9.

TABLE 9

| | Compound | Infrared ray absorption spectrum | Elemental analysis (%) found value (calculated value) | Ultraviolet ray absorption spectrum (in dioxane) | Nuclear magnetic resonance spectrum ($\delta$) | Mass spectrum (m/e) |
|---|---|---|---|---|---|---|
| Example 50 | 1-{4-(1-t-amylperoxy-1-methylethyl)phenyl}-2-hydroxy-2-methyl propan-1-one | 870 cm$^{-1}$ (O—O bond) 1660 cm$^{-1}$ (C=O bond) 3450 cm$^{-1}$ (O—H bond) | C; 70.08 (70.10) H; 9.14 (9.15) | 258 nm ($\epsilon$ 16000) 321 nm ($\epsilon$ 113) | 0.90 ppm (3H) 1.20 ppm (6H) 1.54 ppm (2H) 1.62 ppm (12H) 4.15 ppm (1H) 7.4–8.4 ppm (4H) | 308 |
| Example 51 | 1-{4-(1-t-hexylperoxy-1-methylethyl)phenyl}-2-hydroxy-2-methyl propan-1-one | 870 cm$^{-1}$ (O—O bond) 1660 cm$^{-1}$ (C=O bond) 3450 cm$^{-1}$ (O—H bond) | C; 70.74 (70.77) H; 9.37 (9.38) | 257 nm ($\epsilon$ 16400) 322 nm ($\epsilon$ 105) | 0.90 ppm (3H) 1.20 ppm (6H) 1.54 ppm (4H) 1.62 ppm (12H) 4.20 ppm (1H) 7.4–8.4 ppm (4H) | 322 |
| Example 52 | 1-{4-(1-t-octylperoxy-1-methylethyl)phenyl}-2-hydroxy-2-methyl propan-1-one | 870 cm$^{-1}$ (O—O bond) 1660 cm$^{-1}$ (C=O bond) 3450 cm$^{-1}$ (O—H bond) | C; 71.96 (71.96) H; 9.77 (9.78) | 258 nm ($\epsilon$ 16200) 322 nm ($\epsilon$ 104) | 1.02 ppm (12H) 1.22 ppm (6H) 1.55 ppm (2H) 1.63 ppm (12H) 4.20 ppm (1H) 7.3–8.2 ppm (4H) | 350 |
| Example 53 | 1-{4-(1-cumylperoxy-1-methylethyl)phenyl}-2-hydroxy-2-methyl propan-1-one | 870 cm$^{-1}$ (O—O bond) 1660 cm$^{-1}$ (C=O bond) 3450 cm$^{-1}$ (O—H bond) | C; 74.10 (74.13) H; 7.90 (7.92) | 254 nm ($\epsilon$ 17000) 324 nm ($\epsilon$ 110) | 1.62 ppm (18H) 4.18 ppm (1H) 7.4–8.4 ppm (9H) | 356 |
| Example 54 | 1-{4-(1-t-butylperoxy-1-methylethyl)-2,6-diisopropyl phenyl}-2-hydroxy-2-methyl propan-1-one | 870 cm$^{-1}$ (O—O bond) 1660 cm$^{-1}$ (C=O bond) 3450 cm$^{-1}$ (O—H bond) | C; 72.95 (72.98) H; 10.11 (10.12) | 260 nm ($\epsilon$ 18000) 323 nm ($\epsilon$ 123) | 1.16 ppm (12H) 1.20 ppm (9H) 160 ppm (12H) 3.12 ppm (2H) 4.20 ppm (1H) 7.6 ppm (2H) | 378 |
| Example 55 | 1-{3-(1-t-butylperoxy-1-methylethyl)-6-methyl phenyl}-2-hydroxy-2-methyl propan-1-one | 870 cm$^{-1}$ (O—O bond) 1660 cm$^{-1}$ (C=O bond) 3450 cm$^{-1}$ (O—H bond) | C; 70.06 (70.10) H; 9.13 (9.15) | 257 nm ($\epsilon$ 16100) 321 nm ($\epsilon$ 98) | 1.22 ppm (9H) 1.61 ppm (12H) 2.38 ppm (3H) 4.18 ppm (1H) 4.18 ppm (1H) 7.3–8.2 ppm (3H) | 308 |
| Example 56 | 1-{4-(1-t-butylperoxy-1-methylethyl)benzoyl}-1-hydroxy cyclohexane | 870 cm$^{-1}$ (O—O bond) 1660 cm$^{-1}$ (C=O bond) 3450 cm$^{-1}$ (O—H bond) | C; 71.80 (71.82) H; 9.03 (9.04) | 259 nm ($\epsilon$ 16300) 322 nm ($\epsilon$ 120) | 1.20 ppm (9H) 1.2–1.7 ppm (12H) 1.83 ppm (4H) 4.21 ppm (1H) 7.4–8.2 ppm (4H) | 334 |

EXAMPLE 57

Into a four-necked flask of 100 ml provided with a stirrer and a thermometer was charged a suspension of 14.3 g (0.05 mol) of p-(α-hydroxyisopropyl)-α-bromoisobutyro phenone, 5.0 g (0.055 mol) of t-butyl hydroperoxide and 0.2 g of magnesium sulfate, to which was added dropwise 5.0 g (0.0005 mol) of a solution of 1% perchloric acid in acetic acid while maintaining temperature below 25° C., and the stirring was continued for 2 hours after the temperature was raised to 40° C. After the cooling, the reaction mixture was washed with an aqueous solution of 5% sodium hydroxide and further with water, dried on anhydrous magnesium sulfate, and after the solvent was removed off, the residue was crystallized in methanol or subjected to column chromatography to obtain 14.2 g of a white solid. As result of the same analyses as in Example 39, the resulting compound was confirmed to be 1-{4-(1-t-butylperoxy-1-methylethyl) phenyl]-2-bromo-2-methyl propan-1-one.

EXAMPLE 58

Into a four-necked flask of 100 ml provided with a stirrer and a thermometer was charged a solution of 13.4 g (0.05 mol) of p-isopropenyl-α-bromoisobutyro phenone in isopropyl alcohol, to which were added dropwise 1.0 g (0.01 mol) of concentrated hydrochloric acid and further 5.0 g (0.055 mol) of t-butyl hydroperoxide while maintaining temperature below 25° C. and the stirring was continued for 2 hours after the temperature was raised to 40° C. After the cooling, the reaction mixture was washed with an aqueous solution of 5% sodium hydroxide and further with water, dried on magnesium sulfate, and after the solvent was removed off, the residue was crystallized in methanol or subjected to column chromatography to obtain 13.7 g of a white solid. As a result of the same analyses as in Example 39, the resulting compound was confirmed to be 1-[4-(1-t-butylperoxy-1-methylethyl) phenyl-2-bromo-2-methyl propan-1-one.

EXAMPLE 59

Into a four-necked flask of 200 ml provided with a stirrer and a thermometer were charged 12.5 g (0.125 mol) of an aqueous solution of 40% sodium hydroxide, 25 g of benzene and 75 g of dioxane with stirring, to which were added 11.3 g (0.125 mol) of t-butyl hydroperoxide and 34.8 g (0.10 mol) of p-(α-bromoisopropyl)-α-bromoisobutyro phenone while cooling on ice at 3°–6° C. Thereafter, the reaction was continued at 5° C. for 6 hours. The organic phase was taken out from the resulting reaction mixture, washed with 10% sodium hydroxide 2 times and with saturated saline water 2 to 3 times, dried on anhydrous magnesium sulfate, and after the solvent was removed off, the residue was crystallized in methanol or subjected to column chromatography to obtain 19.2 g of a white solid. As a result of the same analyses as in Example 39, the resulting compound was confirmed to be 1-{4-(1-t-butylperoxy-1-methylethyl) phenyl}-2-hydroxy-2-methyl propan-1-one.

EXAMPLE 60

The same procedure as in Example 57 was repeated except that t-butyl alcohol and p-(α-hydroperoxyisopropyl)-α-methoxyisobutyro phenone were used instead of p-(α-hydroxyisopropyl)-α-bromoisobutyro phenone, and the same analyses as in Example 39 were conducted, from which the resulting compound was confirmed to be 1-{4-(1-t-butylperoxy-1-methylethyl) phenyl}-2-methoxy-2-methyl propan-1-one.

EXAMPLE 61

The same procedure as in Example 58 was repeated Example 61 except that 2-methyl-1-pentene and p-(α-hydroperoxyisopropyl)-α-methoxyisobutyro phenone were used instead of p-isopropenyl-α-bromoisobutyro phenone and t-butyl hydroperoxide, and the same analyses as in Example 39 were conducted, from which the resulting compound was confirmed to be 1-[4-(1-t-hexylperoxy-1-methylethyl) phenyl-2-methoxy-2-methyl propan 1-one.

EXAMPLE 62

The same procedure as in Example 59 was repeated except that t-butyl chloride and p-(α-hydroperoxyisopropyl)-α-methoxyisobutyro phenone were used instead of p-(α-bromoisopropyl)-α-bromoisobutyro phenone and t-butyl hydroperoxide, and the same analyses as in Example 39 were conducted, from which the resulting compound was confirmed to be 1-[4-(1-t-butylperoxy-1-methylethyl) phenyl]-2-methoxy-2-methyl propan-1-one.

EXAMPLES 63-82

Into a quartz tube for photopolymerization were charged given amounts of methyl methacrylate containing no polymerization inhibitor and the photopolymerization initiator according to the invention. After the inside of the tube was replaced with nitrogen by freeze-thaw process, the tube was placed in a thermostatic chamber and a ultraviolet ray of 365 nm was irradiated thereto at a distance of 8 cm through a high pressure mercury lamp of 400 W (using a filter of UVT36A) by means of a merry-go-round type light irradiating device (made by Oshina Kogyo K.K., trade name: MGR-P model) for 30 minutes. Then, the degree of conversion and polymerization rate ($R_p$) were measured by a gravimetry based on methanol settling process. The measured results are shown in the following Table 10.

COMPARATIVE EXAMPLE 1

Methyl methacrylate was polymerized in the same manner as in Example 63 except that a given amount of the conventional photopolymerization initiator shown in Table 4 was used in stead of the photopolymerization initiator according to the invention, and then the degree of conversion and the polymerization rate were measured. The measured results ar also shown in Table 10.

TABLE 10

| | Photopolymerization initiator | Amount of initiator added (mol/l) | Degree of conversion after 30 minutes (%) | Initial polymerization rate $R_p \times 10^2$ (mol/l.s) |
|---|---|---|---|---|
| Example 63 | 4-(1-t-butylperoxy-1-methylethyl) benzophenone | 0.01 | 14.3 | 8.5 |
| Example 64 | 4-(1-t-amylperoxy-1-methylethyl) benzophenone | 0.01 | 14.3 | 8.5 |
| Example 65 | 4-(1-t-hexylperoxy-1-methylethyl) benzophenone | 0.01 | 14.1 | 8.4 |
| Example 66 | 4-(1-t-octylperoxy-1-methylethyl) benzophenone | 0.01 | 14.0 | 8.3 |
| Example 67 | 4-(1-cumylperoxy-1-methylethyl) benzophenone | 0.005 | 14.4 | 8.5 |
| Example 68 | 4,4'-bis(1-t-butylperoxy-1-methylethyl) benzophenone | 0.005 | 16.4 | 10.7 |
| Example 69 | 4,4'-bis(1-t-amylperoxy-1-methylethyl) benzophenone | 0.005 | 16.5 | 10.7 |
| Example 70 | 4,4'-bis(1-t-hexylperoxy-1-methylethyl) benzophenone | 0.005 | 16.1 | 10.5 |
| Example 71 | 4,4'-bis(1-t-octylperoxy-1-methylethyl) benzophenone | 0.005 | 16.4 | 10.6 |
| Example 72 | 4,4'-bis(1-cumylperoxy-1-methylethyl) benzophenone | 0.005 | 15.9 | 10.4 |
| Example 73 | 3,4'-bis(1-t-butylperoxy-1-methylethyl)-6-methyl benzophenone | 0.005 | 14.4 | 9.4 |

TABLE 10-continued

| | Photopolymerization initiator | Amount of initiator added (mol/l) | Degree of conversion after 30 minutes (%) | Initial polymerization rate $R_p \times 10^2$ (mol/l.s) |
| --- | --- | --- | --- | --- |
| Example 74 | 3,3'-bis(1-t-butylperoxy-1-methylethyl)-6-methyl benzophenone | 0.005 | 13.3 | 8.5 |
| Example 75 | 1-{4-(1-t-butylperoxy-1-methylethyl)phenyl}-2-bromo-2-methyl propan-1-one | 0.01 | 17.7 | 9.5 |
| Example 76 | 1-{4-(1-t-butylperoxy-1-methylethyl)peroxy}-2-bromo-2-methyl propan-1-one | 0.005 | 13.9 | 7.5 |
| Example 77 | 1-{4-(1-t-butylperoxy-1-methylethyl)phenyl}-2-methoxy-2-methyl propan-1-one | 0.01 | 16.5 | 8.9 |
| Example 78 | 1-{4-(1-t-butylperoxy-1-methylethyl)phenyl}-2-methoxy-2-methyl propan-1-one | 0.005 | 12.6 | 6.6 |
| Example 79 | 1-{4-(1-t-butylperoxy-1-methylethyl)phenyl}-2-hydroxy-2-methyl propan-1-one | 0.01 | 19.4 | 10.5 |
| Example 80 | 1-{4-(1-t-butylperoxy-1-methylethyl)phenyl}-2-hydroxy-2-methyl propan-1-one | 0.005 | 14.7 | 7.7 |
| Example 81 | 1-{3-(1-t-butylperoxy-1-methylethyl)-6-methylphenyl}-2-hydroxy-2-methyl propan-1-one | 0.01 | 18.1 | 9.8 |
| Example 82 | 1-{3-(1-t-butylperoxy-1-methylethyl)-6-methylphenyl}-2-hydroxy-2-methyl propan-1-one | 0.005 | 14.1 | 7.4 |
| Comparative Example 1 | 2-hydroxy-2-methyl-1-phenyl propan-1-one (1) | 0.01 | 14.8 | 7.7 |

(1) Darocure 1173, trade name, made by Merck Co.

The results in Table 10 show that the compounds according to the invention have an effective photopolymerization performance.

EXAMPLES 83–85

To methyl methacrylate was added 0.1 mol/l of 4-(1-t-butylperoxy-1-methylethyl) benzophenone, 0.005 mol/l of 4,4'-bis(1-t-butylperoxy-1-methylethyl) benzophenone or 0.01 mol/l of 1-(4-(1-t-butylperoxy-1-methylethyl) phenyl]-2-hydroxy-2-methyl prop according to the invention, which was polymerized by varying the light irradiating time in the same manner as in Example 63, whereby the degree of conversion was measured. The relation between the irradiating time and the degree of conversion measured is shown in FIG. 1.

COMPARATIVE EXAMPLE 2

Methyl methacrylate was polymerized in the same manner as in Example 83 except that 0.01 mol/l of the conventional photopolymerization initiator shown in Table 4 was used instead of the photopolymerization initiator according to the invention, and the relation between irradiating time and degree of conversion measured is also shown in FIG. 1.

As seen from FIG. 1, the use of the photopolymerization initiator according to the invention exhibits a large polymerization activity.

EXAMPLES 8614 90

Onto a glass plate was applied an ester acrylate resin (a composition of Aronix M-8060 (trade name, made by Toa Gosei K.K.)/Aronix M-5700 (trade name, made by Toa Gosei K.K.) as a mixing ratio of 4/6) containing 2 parts by weight of 4-(1-t-butylperoxy-1-methylethyl) benzophenone, 4,4'-bis(1-t-butylperoxy-1-methylethyl) benzophenone, 1-{4-(1-t-butylperoxy-1-methylethyl) phenyl]-2-bromo-2-methyl propan-1-one, 1-14-(1-t-butylperoxy-1-methylethyl) phenyl)-2-methyl propan-1-one or 1-[4-(1-t-butylperoxy-1-methylethyl phenyl]2-hydroxy-2-methyl propan-1-one according to the invention at a thickness of 100 mµ, which was cured by means of a conveyor type ultraviolet-ray curing device (focusing type). In any case, the cured resin was not yellowed visually.

COMPARATIVE EXAMPLE 3

The ester acrylate resin was cured in the same manner as in Example 86 except that 1,2-diphenyl-2,2-dimethoxy ethan-1-one was used instead of the photopolymerization initiator according to the invention. The cured resin was yellowed.

EXAMPLES 91–106

Into a glass bottle was charged an ester acrylate resin (the same composition as in Example 86) containing 2 parts by weight of the photopolymerization initiator according to the invention, which was placed in an incubator at 60° C. to measure a storing stability in dark room. The measured results were indicated by the number of days visually observing gelation. The storing stability in dark room measured is shown in the following Table 11.

COMPARATIVE EXAMPLES 4-6

The storing stability in dark room was measured in the same manner as in Example 91 except that the conventional photopolymerization initiators shown in Table 11 were used instead of the photopolymerization initiator according to the invention. The measured results are also shown in Table 11.

TABLE 11

| | Photopolymerization initiator | Storing stability in dark room (days) |
|---|---|---|
| Example 91 | 4-(1-t-butylperoxy-1-methylethyl) benzophenone | >100 |
| Example 92 | 4-(1-t-amylperoxy-1-methylethyl) benzophenone | >100 |
| Example 93 | 4-(1-t-hexylperoxy-1-methylethyl) benzophenone | >100 |
| Example 94 | 4-(1-t-octylperoxy-1-methylethyl) benzophenone | >100 |
| Example 95 | 4-(1-cumylperoxy-1-methylethyl) benzophenone | >100 |
| Example 96 | 4,4'-bis(1-t-butylperoxyl-1-methylethyl) benzophenone | >100 |
| Example 97 | 4,4'-bis(1-t-amylperoxy-1-methylethyl) benzophenone | >100 |
| Example 98 | 4,4'-bis(1-t-hexylperoxy-1-methylethyl) benzophenone | >100 |
| Example 99 | 4,4'-bis(1-t-octylperoxy-1-methylethyl) benzophenone | >100 |
| Example 100 | 4,4'-bis(1-cumylperoxyl-1-methylethyl) benzophenone | >100 |
| Example 101 | 3,4'-bis(1-t-butylperoxy-1-methylethyl)-6-methyl benzophenone | >100 |
| Example 102 | 3,3'-bis(1-t-butylperoxy-1-methylethyl)6-methyl benzophenone | >100 |
| Example 103 | 1-{4-(1-t-butylperoxy-1-methylethyl) phenyl}-2-bromo-2-methyl propane-1-on | >100 |
| Example 104 | 1-{4-(1-t-butylperoxy-1-methylethyl) phenyl}-2-methoxy-2-methyl propane-1-on | >100 |
| Example 105 | 1-{4-(1-t-butylperoxy-1-methylethyl) phenyl}-2-hydroxy-2-methyl propane-1-on | >100 |
| Example 106 | 1-{3-(1-t-butylperoxy-1-methylethyl)-6-methylethyl}-2-hydroxy-2-methyl propane-1-on | >100 |
| Comparative Example 4 | benzoisobutyl ether | 5 |
| Comparative Example 5 | 1,2-diphenyl-2,2-dimethoxyethan-1-one (1) | 90 |
| Comparative Example 6 | 2-hydroxy-2-methyl-1-phenyl propan-1-one (2) | >100 |

(1) Irgacure 651, trade name, made by Ciba Geigy
(2) Darocure 1173, trade name, made by Merck Co.

EXAMPLES 107-110

Into a glass ampule tube of 20 ml capacity was placed 10 g of styrene containing a given amount of the compound according to the invention. After the deaeration under vacuum, the tube was sealed. This tube was placed in a thermostatic oil chamber of 120° C. to conduct polymerization for a given time. The resulting polymer was poured into methanol to conduct reprecipitation and then the degree of conversion was calculated from the weight of the resulting white powder. Furthermore, the weight average molecular weight (Mw) was measured by gel permeation chromatography (GPC). The results are shown in the following Table 12.

COMPARATIVE EXAMPLE 7

The polymerization was carried out in the same manner as in Example 107 except that 0.005 mol/l of t-butyl cumyl peroxide was used instead of the compound according to the invention. The results are also shown in Table 12.

TABLE 12

| Organic peroxide Concentration (mol/l) | Example 107 4-(t-butylperoxy-1-methylethyl) benzophenone 0.005 | | Example 108 4,4'-bis(t-butylperoxy-1-methylethyl) benzophenone 0.0025 | | Example 109 1-{4-(1-t-butylperoxy-1-methylethyl)phenyl}-2-bromo-2-methyl propan-1-one 0.005 | | Example 110 1-{4-(1-t-butylperoxy-1-methylethyl)phenyl}-2-hydroxyl-2-methyl propan-1-one 0.005 | | Comparative Example 7 t-butyl cumyl peroxide 0.005 | |
|---|---|---|---|---|---|---|---|---|---|---|
| Polymerization time (hr) | Degree of conversion (%) | Mw × $10^{-4}$ | Degree of conversion (%) | Mw × $10^{-4}$ | Degree of conversion (%) | Mw × $10^{-4}$ | Degree of conversion (%) | Mw × $10^{-4}$ | Degree of conversion (%) | Mw × $10^{-4}$ |
| 1 | 18.9 | 31.6 | 18.8 | 50.6 | 17.7 | 32.6 | 18.1 | 32.2 | 18.6 | 31.8 |
| 2 | 35.3 | 31.8 | 35.2 | 52.7 | 33.1 | 33.3 | 33.9 | 32.9 | 34.9 | 32.1 |
| 3 | 52.8 | 33.1 | 53.0 | 58.2 | 49.7 | 34.3 | 50.9 | 33.9 | 51.4 | 33.5 |
| 4 | 73.8 | 38.6 | 73.6 | 65.5 | 71.5 | 40.1 | 72.0 | 39.9 | 72.3 | 39.4 |
| 5 | 89.9 | 41.4 | 89.5 | 79.4 | 87.1 | 44.4 | 87.3 | 43.8 | 87.8 | 43.6 |

As seen from Table 12, the compound according to the invention has an effective performance as a thermal polymerization initiator.

EXAMPLES 111-114

Into a Henschel mixer of 75 l capacity (stirring blade: standard type) were simultaneously charged 20 kg of powdery polyethylene having an apparent specific gravity of 0.45, a particle size of 99.5% pass through ASTM 30 mesh, MI of 30.5 and a density of 0.956 and 0.2 kg of the compound according to the invention, which were mixed at about 750 rpm for 2 minutes and at 1500 rpm for 8 minutes.

The resulting mixture was fed to a casting mold to obtain a desired product through biaxial rotation shaping process. The appearance and mechanical properties of the obtained product are shown in the following Table 13.

COMPARATIVE EXAMPLE 8

The same procedure as in Example 111 was repeated except that dicumyl peroxide was used instead of the compound according to the invention, and the same measurement in Example 111 was made to obtain results as shown in Table 13.

TABLE 13

| Organic peroxide | Example 111 4-(1-t-butylperoxy-1-methylethyl) benzophenone | Example 112 4,4'-bis(1-t-butylperoxy-1-methylethyl) benzophenone | Example 113 1-{4-(1-t-butylperoxy-1-methylethyl)phenyl}-2-bromo-2-methyl propan-1-one | Example 114 1-{4-(1-t-butylperoxy-1-methylethyl)phenyl}-2-hydroxy-2-methyl propan-1-one | Comparative Example 8 dicumyl peroxide |
|---|---|---|---|---|---|
| Yield strength ($Kg/cm^2$) D-638 | 170 | 200 | 160 | 170 | 180 |
| Elongation at break ASTM (%) D-638 | >500% | >500% | >500% | >500% | >500% |
| Impact strength ASTM ($Kg\text{-}cm/cm^2$) D-1822 (20° C.) | 460 | 500 | 440 | 450 | 430 |

What is claimed is:

1. A dialkyl peroxide represented by the following general formula (I):

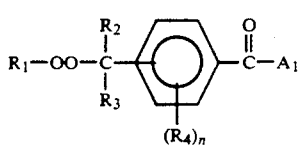
(I)

wherein

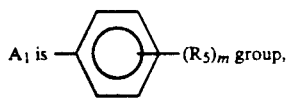

—$C(R_9)(R_{10})(Z_1)$ group, each of $R_1$ and $R_6$ is a tertiary alkyl group having a carbon number of 4–8 or an α-cumyl group, each of $R_2$, $R_3$, $R_7$ and $R_8$ is an alkyl group having a carbon number of 1–2, $R_4$ is an alkyl group having a carbon number of 1–3 or a hydrogen atom, $R_5$ is an alkyl group having a carbon number of 1–12, an alkoxy group having a carbon number of 1–4, a halogen atom or a hydrogen atom, each of $R_9$ and $R_{10}$ is an alkyl group having a carbon number of 1–4 or $R_9$ and $R_{10}$ form a cycloalkyl group having a total carbon number of 5–8 together, $Z_1$ is a hydroxyl group, a chlorine atom, a bromine atom or an alkoxy group having a carbon number of 1–4, n is 1 or 2, m is an integer of 1–3, and each of $R_1OOC(R_2)(R_3)$ group and $R_6OOC(R_7)(R_8)$ group is a meta or para position).

2. A photolysis type radical forming agent comprising as an effective ingredient a dialkyl peroxide represented by the following general formula (I):

(I)

wherein $A_1$ is 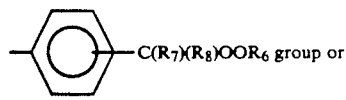 group,

—$C(R_9)(R_{10})(Z_1)$ group, each of $R_1$ and $R_6$ is a tertiary alkyl group having a carbon number of 4–8 or an α-cumyl group, each of $R_2$, $R_3$, $R_7$ and $R_8$ is an alkyl group having a carbon number of 1–2, $R_4$ is an alkyl group having a carbon number of 1–3 or a hydrogen atom, $R_5$ is an alkyl group having a carbon number of 1–12, an alkoxy group having a carbon number of 1–4, a halogen atom or a hydrogen atom, each of $R_9$ and $R_{10}$ is an alkyl group having a carbon number of 1–4 or $R_9$ and $R_{10}$ form a cycloalkyl group having a total carbon number of 5–8 together, $Z_1$ is a hydroxyl group, a chlorine atom, a bromine atom or an alkoxy group having a carbon number of 1–4, n is 1 or 2, m is an integer of 1–3, and each of $R_1OOC(R_2)(R_3)$ group and $R_6OOC(R_7)(R_8)$ group is a meta or para position).

3. A pyrolysis type radical forming agent comprising as an effective ingredient a dialkyl peroxide represented by the following general formula ():

(I)

wherein $A_1$ is 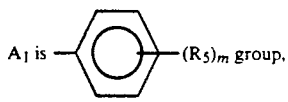 group,

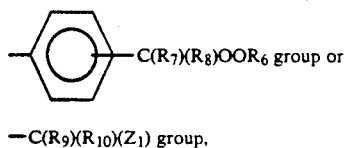 group or

—$C(R_9)(R_{10})(Z_1)$ group, each of $R_1$ and $R_6$ is a tertiary alkyl group having a carbon number of 4-8 or an α-cumyl group, each of $R_2$, $R_3$, $R_7$ and $R_8$ is an alkyl group having a carbon number of 1-2, $R_4$ is an alkyl group having a carbon number of 1-3 or a hydrogen atom, $R_5$ is an alkyl group having a carbon number of 1-12, an alkoxy group having a carbon number of 1-4, a halogen atom or a hydrogen atom, each of $R_9$ and $R_{10}$ is an alkyl group having a carbon number of 1-4 or $R_9$ and $R_{10}$ form a cycloalkyl group having a total carbon number of 5-8 together, $Z_1$ is a hydroxyl group, a chlorine atom, a bromine atom or an alkoxy group having a carbon number of 1-4, n is 1 or 2, m is an integer of 1-3, and each of $R_1OOC(R_2)(R_3)$ group and $R_6OOC(R_7)(R_8)$ group is a meta or para position).

* * * * *